(12) United States Patent
Huang et al.

(10) Patent No.: US 8,409,632 B2
(45) Date of Patent: Apr. 2, 2013

(54) **PRODUCT CONTAINING EXTRACT FROM *ZANTHOXYLUM AVICENNAE* (LAM.) DC., AND PREPARATION PROCESS AND USE THEREOF**

(75) Inventors: Chih-Yang Huang, Taichung (TW); Duc-Dung Tran, Taichung (TW); Jer-Yuh Liu, Taichung (TW)

(73) Assignee: China Medical University, Taichung (TW)

( * ) Notice: Subject to any disclaimer, the term of this patent is extended or adjusted under 35 U.S.C. 154(b) by 205 days.

(21) Appl. No.: 13/014,106

(22) Filed: Jan. 26, 2011

(65) Prior Publication Data

US 2011/0183014 A1   Jul. 28, 2011

Related U.S. Application Data

(60) Provisional application No. 61/368,958, filed on Jul. 29, 2010.

(30) Foreign Application Priority Data

Jan. 28, 2010   (TW) .............................. 99102417 A
Jun. 3, 2010    (TW) .............................. 99117914 A

(51) Int. Cl.
*A61K 36/00* (2006.01)
(52) U.S. Cl. ...................................................... 424/725
(58) Field of Classification Search ........................ None
See application file for complete search history.

(56) References Cited

U.S. PATENT DOCUMENTS

| 6,743,930 | B2 * | 6/2004 | Li ................................... 554/12 |
| 2003/0198732 | A1 * | 10/2003 | Wang ............................ 426/643 |
| 2010/0137822 | A1 * | 6/2010 | Chen ............................ 604/359 |
| 2011/0045109 | A1 * | 2/2011 | Fowler et al. ................. 424/769 |

FOREIGN PATENT DOCUMENTS

| CN | 1616058 | * | 5/2005 |
| CN | 1772088 | * | 5/2006 |
| CN | 101129946 | * | 2/2008 |
| CN | 101254156 | * | 9/2008 |
| CN | 101623469 | * | 1/2010 |
| CN | 101991770 | * | 3/2011 |

OTHER PUBLICATIONS

Arthur et al. J. Chem. Soc. 1956. pp. 632-635.*

* cited by examiner

*Primary Examiner* — Christopher R. Tate
(74) *Attorney, Agent, or Firm* — Occhiuti Rohlicek & Tsao LLP

(57) ABSTRACT

Disclosed herein are a product containing an extract from *Zanthoxylum avicennae* (Lam.) DC. and a process for preparing the same. Also disclosed herein are a pharmaceutical composition including the aforesaid product containing the extract from *Zanthoxylum avicennae* (Lam.) DC., a method of treating a cancer in a subject via the aforementioned pharmaceutical composition, and a method of inhibiting tumor/cancer cells by virtue of the aforesaid product containing the extract from *Zanthoxylum avicennae* (Lam.) DC.

14 Claims, 26 Drawing Sheets

PRODUCT CONTAINING EXTRACT FROM ZANTHOXYLUM AVICENNAE (LAM.) DC., AND PREPARATION PROCESS AND USE THEREOF

CROSS-REFERENCE TO RELATED APPLICATIONS

This application claims priority of Taiwanese application no. 099102417, filed on Jan. 28, 2010, and Taiwanese application no. 099117914, filed on Jun. 3, 2010. This application also claims priority of U.S. provisional application No. 61/368,958, filed on Jul. 29, 2010.

BACKGROUND OF THE INVENTION

1. Field of the Invention

This invention relates to a product containing an extract from Zanthoxylum avicennae (Lam.) DC. and a preparation process thereof. This invention also relates to a pharmaceutical composition which comprises the product containing the extract from Zanthoxylum avicennae (Lam.) DC.

2. Description of the Related Art

Cancer is one of the leading causes of human death nowadays. Particularly, liver cancer is one of the most common types of cancer. The mechanism of carcinogenesis has not been completely understood. However, carcinogenesis can be attributed to the following reason. When genetic abnormalities are induced by exogenous or endogenous factors with respect to cells, signal transduction in the cells may become abnormal, thereby further giving rise to uncontrolled cell division. Cancer cells are accordingly formed. Furthermore, the cancer cells may continuously proliferate and may metastasize to other portions of the body through the lymphatic system or the vascular system.

Generally speaking, deactivation of the apoptosis signal transduction pathway (e.g., the death receptor-dependent apoptosis signal transduction pathway and the mitochondria-dependent apoptosis signal transduction pathway) and/or activation of the cell survival signal transduction pathway may result in proliferation of cancer cells. In addition, activation of the urokinase plasminogen activator signal transduction pathway, the mitogen-activated protein kinase (MAPK) signal transduction pathway, or the β-catenin signal transduction pathway may lead to metastasis of cancer cells. Therefore, in recent years, research in inhibiting proliferation and metastasis of cancer cells, and inducing apoptosis of cancer cells, by virtue of deactivation and/or activation of the aforesaid signal transduction pathways has become important for developing an anticancer drug.

Effects of the conventional anticancer drugs on cancer are unsatisfactory basically due to individual differences of patients, severe side effects thereof, and drug resistance of cancer cells. In view of the foregoing, some researchers have attempted to find active components, which can be used in cancer treatment, from traditional Chinese medicine (TCM).

Zanthoxylum avicennae (Lam.) DC. (trivial name: avicennia pricklyash; YING BU BO in pinyin) is a perennial evergreen shrub or an arbor which belongs to Rutaceae, and the trunk and the branch thereof have reddish brown prickles. Zanthoxylum avicennae (Lam.) DC. can be found in Taiwan, China, Vietnam, Laos, Cambodia, etc. It is reported that each portion of Zanthoxylum avicennae (Lam.) DC. (e.g., a root, a stem, a leaf, fruit, etc.) is wholesome or has a therapeutic effect (Nanjing University of Chinese Medicine, Dictionary of Chinese Materia Medica, Shanghai Scientific and Technical Publisher, 2006, $2^{nd}$ edition, Volume 2, pages 3824-3825).

It is recorded that: the fruit of Zanthoxylum avicennae (Lam.) DC. has therapeutic effects on stomachache and abdominal pain; the leaf of Zanthoxylum avicennae (Lam.) DC. has therapeutic effects on bone-setters injury, strain of lumbar muscles, mastadenitis, and swollen boil; and the root of Zanthoxylum avicennae (Lam.) DC. has therapeutic effects on icterohepatitis, jaundice edema, hepatitis B, hepatocirrhosis, edema due to nephritis, bone-setters injury, rheumatoid arthritis, strain of lumbar muscles, leucorrhea, common cold, sore throat, cough, malaria, colitis, and stomatitis (Bian Xie Zu, Meaning Whole China Herb Conglomeration Edition, Journal of People's Public Health, 1975, $1^{st}$ edition, Volume 1, pages 928; Lan-Chang Zhang, Dictionary of Chinese Herbs, Chao Ren Press, 1981, Volume 5, pages 5513-5514; Nanjing University of Chinese Medicine, Dictionary of Chinese Materia Medica, Shanghai Scientific and Technical Publisher, 2006, $2^{nd}$ edition, Volume 2, pages 3824-3825).

The following experiment was conducted by T. T. Thuy et al. [T. T. Thuy et al. (1999), Phytochemistry, 50:903-907]. The leaf of Zanthoxylum avicennae (Lam.) DC. was subjected to an extraction treatment using 95% MeOH at room temperature, and MeOH was removed by virtue of distillation under vacuum. The resultant aqueous solution was extracted with n-hexane, followed by EtOAc and n-BuOH. n-BuOH was removed under vacuum, and the residue was subsequently subjected to partitioning using $CHCl_3$ and $H_2O$. The $CHCl_3$ layer was collected, followed by removing $CHCl_3$ under vacuum so as to obtain an extract from the leaf of Zanthoxylum avicennae (Lam.) DC. The extract from the leaf of Zanthoxylum avicennae (Lam.) DC. was further subjected to isolation and purification, thereby acquiring three novel alkaloids, i.e., (−)-culantraramine N-oxide, (−)-culantraraminol N-oxide, and avicennamine.

J. J. Chen et al. reported that: in a previous study, an extract from the stem wood of Zanthoxylum avicennae (Lam.) DC. was prepared by the process including subjecting the stem wood of Zanthoxylum avicennae (Lam.) DC. to an extraction treatment with cold MeOH, concentrating the resultant product under reduced pressure, conducting a partitioning treatment with EtOAc and $H_2O$, and collecting the thus formed EtOAc-soluble fraction [J. J. Chen et al. (2008), Journal of Natural Products, 71:212-217]. The extract from the stem wood of Zanthoxylum avicennae (Lam.) DC. was proven to be able to suppress FMLP/CB (formyl-L-methionyl-L-leucyl-L-phenylalanine/cytochal-asin B)-induced superoxide anion generation and elastase release, thereby having anti-inflammatory activity. Accordingly, J. J. Chen et al. further isolated and purified the extract from the stem wood of Zanthoxylum avicennae (Lam.) DC. such that eight new compounds, including four neolignans, a coumarinolignan, two lignan derivatives, and a chromene, were obtained. Furthermore, J. J. Chen et al. evaluated anti-inflammatory effects of the eight compounds on FMLP/CB-induced superoxide anion generation and elastase release.

In order to cure cancer, the applicants have endeavored to investigate activities of Zanthoxylum avicennae (Lam.) DC., and have found that a product containing an extract from Zanthoxylum avicennae (Lam.) DC. is able to inhibit proliferation and metastasis of tumor/cancer cells, and to induce apoptosis of tumor/cancer cells. Furthermore, the product containing the exatract from Zanthoxylum avicennae (Lam.) DC. is also capable of suppressing tumor cell proliferation in vivo and increasing tumor cell apoptosis in vivo. Consequently, the product containing the extract from Zanthoxylum avicennae (Lam.) DC. is expected to be useful in a cancer treatment.

SUMMARY OF THE INVENTION

Therefore, according to a first aspect, this invention provides a product containing an extract from *Zanthoxylum avicennae* (Lam.) DC, which is prepared by a process comprising the steps of:

(a) subjecting a root material of *Zanthoxylum avicennae* (Lam.) DC. to an acid treatment using a first acid solution under heating such that an acid-treated root material of *Zanthoxylum avicennae* (Lam.) DC. is obtained;

(b) subjecting the acid-treated root material of *Zanthoxylum avicennae* (Lam.) DC. to an extraction treatment using an alcohol solution such that an alcohol-extracted product is obtained; and (c) admixing the alcohol-extracted product with a second acid solution such that the product is formed.

According to a second aspect, this invention provides a process for preparing a product containing an extract from *Zanthoxylum avicennae* (Lam.) DC., which comprises the steps of:

(a) subjecting a root material of *Zanthoxylum avicennae* (Lam.) DC. to an acid treatment using a first acid solution under heating such that an acid-treated root material of *Zanthoxylum avicennae* (Lam.) DC. is obtained;

(b) subjecting the acid-treated root material of *Zanthoxylum avicennae* (Lam.) DC. to an extraction treatment using an alcohol solution such that an alcohol-extracted product is obtained; and (c) admixing the alcohol-extracted product with a second acid solution such that the product is formed.

According to a third aspect, this invention provides a pharmaceutical composition comprising the aforementioned product containing the extract from *Zanthoxylum avicennae* (Lam.) DC.

According to a fourth aspect, this invention provides a method of treating a cancer in a subject, which comprises administering to the subject the aforementioned pharmaceutical composition.

According to a fifth aspect, this invention provides a method of inhibiting tumor/cancer cells, which comprises contacting the cells with the aforementioned product containing the extract from *Zanthoxylum avicennae* (Lam.) DC.

BRIEF DESCRIPTION OF THE DRAWINGS

The above and other features and advantages of the present invention will become apparent in the following detailed description of the preferred embodiment with reference to the accompanying drawings, of which.

DETAILED DESCRIPTION OF THE PREFERRED EMBODIMENT

Figure 1:
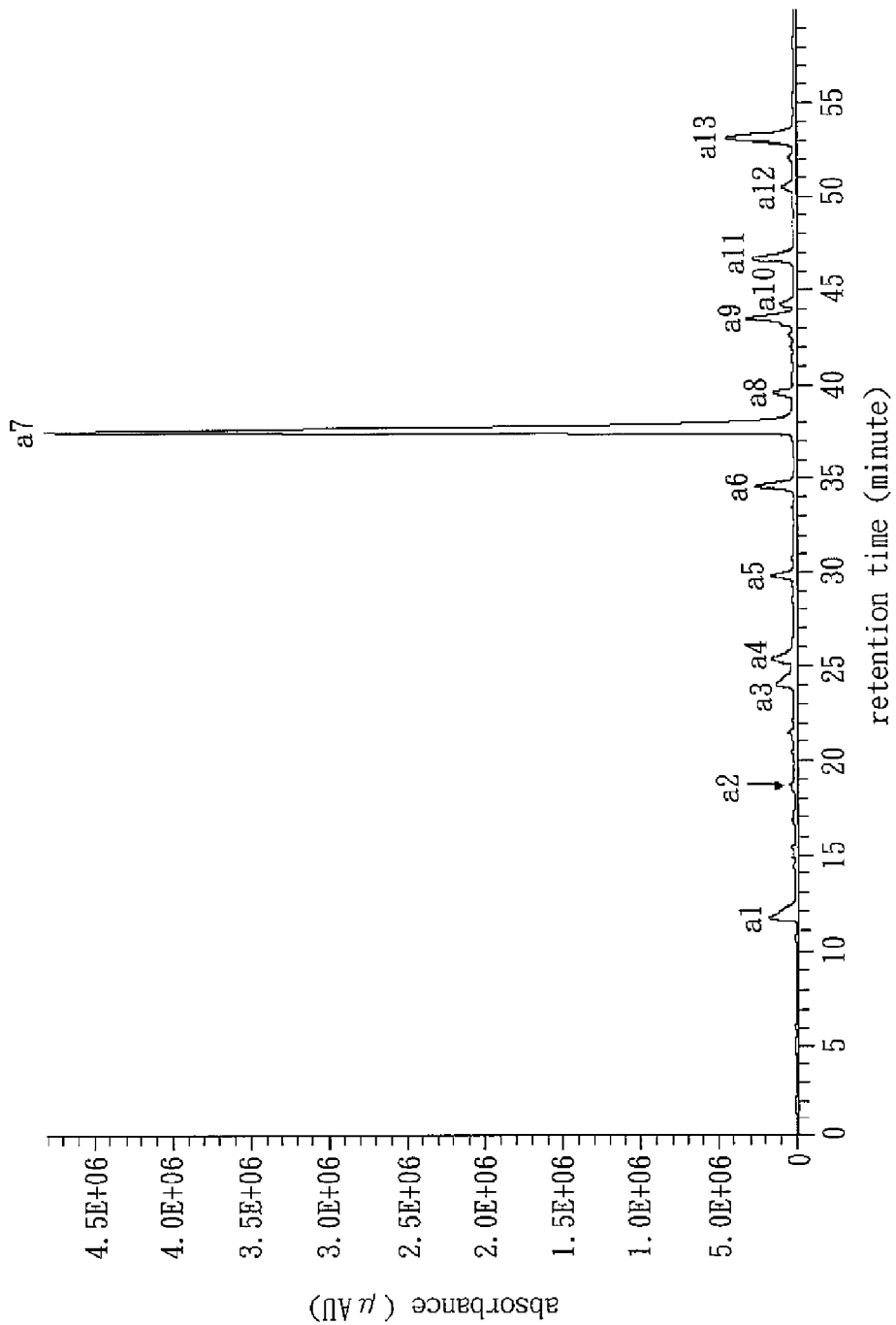
FIG. 1 is a HPLC elution profile of a product containing an extract from *Zanthoxylum avicennae* (Lam.) DC. (designated as PYBBE) prepared according to the Example 1 of this invention.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described.

In order to develop a new drug having an anticancer effect, the applicants have attempted to extract *Zanthoxylum avicennae* (Lam.) DC. using various methods. Eventually, the applicants have successfully obtained a product containing an extract from *Zanthoxylum avicennae* (Lam.) DC., which is effective in inhibiting proliferation and metastasis of tumor/cancer cells and in inducing apoptosis of tumor/cancer cells.

Accordingly, this invention provides a product containing an extract from *Zanthoxylum avicennae* (Lam.) DC., which is prepared by a process comprising the steps of:

(a) subjecting a root material of *Zanthoxylum avicennae* (Lam.) DC. to an acid treatment using a first acid solution under heating such that an acid-treated root material of *Zanthoxylum avicennae* (Lam.) DC. is obtained;

(b) subjecting the acid-treated root material of *Zanthoxylum avicennae* (Lam.) DC. to an extraction treatment using an alcohol solution such that an alcohol-extracted product is obtained; and (c) admixing the alcohol-extracted product with a second acid solution such that the product is formed.

In a preferred embodiment of this invention, the root material of *Zanthoxylum avicennae* (Lam.) DC. is root skin of *Zanthoxylum avicennae* (Lam.) DC.

According to this invention, the first and second acid solutions are independently selected from the group consisting of vinegar, acetic acid, formic acid, lactic acid, malic acid, oxalic acid, and citric acid. Preferably, the first and second acid solutions are vinegar. The vinegar may be fermented vinegar or synthetic vinegar. More preferably, the vinegar is fermented vinegar. The fermented vinegar suitable for this invention includes, but is not limited to, fruit vinegar, grain vinegar, and wine vinegar. The examples of the fruit vinegar include, but are not limited to, banana vinegar, lemon vinegar, apple vinegar, grape vinegar, and orange vinegar. In a preferred embodiment of this invention, the first and second acid solutions are banana vinegar.

According to this invention, the alcohol solution is selected from the group consisting of methanol, ethanol, propanol, isopropanol, n-butanol, and isobutanol. In a preferred embodiment of this invention, the alcohol solution is ethanol.

According to this invention, the product containing the extract from *Zanthoxylum avicennae* (Lam.) DC. may be further subjected to a treatment using a concentrating method (e.g., decompress concentration) and a third acid solution. The third acid solution may be selected from the group consisting of vinegar, acetic acid, formic acid, lactic acid, malic acid, oxalic acid, and citric acid. Preferably, the third acid solution is vinegar. The vinegar may be fermented vinegar or synthetic vinegar. More preferably, the vinegar is fermented vinegar. The fermented vinegar suitable for this invention includes, but is not limited to, fruit vinegar, grain vinegar, and wine vinegar. The examples of the fruit vinegar include, but are not limited to, banana vinegar, lemon vinegar, apple vinegar, grape vinegar, and orange vinegar. In a preferred embodiment of this invention, the third acid solution is banana vinegar.

The product containing the extract from *Zanthoxylum avicennae* (Lam.) DC. according to this invention has been proven to be effective in inhibiting proliferation of tumor/cancer cells, in particular, liver cancer cells. Specifically, the product containing the extract from *Zanthoxylum avicennae* (Lam.) DC. according to this invention is able to reduce the expression of proliferating cell nuclear antigen (PCNA), cyclin A, cyclin D1, cyclin E, cyclin B1, c-Fos, and c-Myc in cells, and to enhance the expression of p21, p27, p-p53, and p53 in cells, thereby being further capable of arresting cells in $G_2/M$ phase of the cell cycle so as to inhibit proliferation of tumor/cancer cells.

In addition, by virtue of cell migration assay and cell invasion assay, the applicants have found that the product containing the extract from *Zanthoxylum avicennae* (Lam.) DC. according to this invention is effective in inhibiting metastasis of tumor/cancer cells, in particular, liver cancer cells. Specifically, the product containing the extract from *Zanthoxylum avicennae* (Lam.) DC. according to this invention is able to inhibit the activation of the urokinase plasminogen activator signal transduction pathway and the β-catenin signal transduction pathway, thereby being capable of inhibiting metastasis of tumor/cancer cells.

Furthermore, by dint of terminal deoxynucleotidyl transferase mediated dUTP nick end labeling (TUNEL), the applicants have found that the product containing the extract from *Zanthoxylum avicennae* (Lam.) DC. according to this invention is effective in inducing apoptosis of tumor/cancer cells, in particular, liver cancer cells. Specifically, the product containing the extract from *Zanthoxylum avicennae* (Lam.) DC. according to this invention is able to activate the death receptor-dependent apoptosis signal transduction pathway and the mitochondria-dependent apoptosis signal transduction pathway, and to induce the depolarization of mitochondrial membrane potential, thereby being capable of inducing apoptosis of tumor/caner cells.

Therefore, this invention provides a method of inhibiting tumor/cancer cells, which comprises contacting the cells with the aforementioned product containing the extract from *Zanthoxylum avicennae* (Lam.) DC. Preferably, the inhibition of tumor/cancer cells includes inhibition of cell proliferation, inhibition of cell metastasis, and induction of apoptosis. Preferably, the tumor/cancer cells to be inhibited are liver cancer cells.

Via an in vivo test, the applicants have found that the product containing the extract from *Zanthoxylum avicennae* (Lam.) DC. according to this invention is able to suppress tumor cell proliferation in vivo and to increase tumor cell apoptosis in vivo. Accordingly, this invention provides a pharmaceutical composition comprising the aforesaid product containing the extract from *Zanthoxylum avicennae* (Lam.) DC.

The pharmaceutical composition according to this invention can be formulated into a suitable dosage form for parenteral, topical, or oral administration using technology well known to those skilled in the art, which includes, but is not limited to, injections (e.g., sterile aqueous solutions or dispersions), sterile powder, tablets, troches, pills, capsules, and the like.

The pharmaceutical composition according to this invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like.

The dosage and the frequency of administration of the pharmaceutical composition according to this invention may vary depending on the following factors: the severity of the disease to be treated, the route of administration, and the weight, age, physical condition and response of the subject to be treated. For instance, the daily dosage of the pharmaceutical composition according to this invention may be 10 to 20 mg per kilogram of the body weight, and may be administered in a single dose or in several doses.

This invention also provides a method of treating a cancer in a subject, which comprises administering to the subject the aforesaid pharmaceutical composition. The aforesaid pharmaceutical composition may be parenterally, orally, or topically administered to the subject. Preferably, the cancer to be treated is liver cancer.

This invention will be further described by way of the following examples. However, it should be understood that the following examples are solely intended for the purpose of illustration and should not be construed as limiting the invention in practice.

EXAMPLES

Experimental Materials:
1. Chang-Liver, Normal Human Liver Cell Line:

Chang-Liver was purchased from Cell Lines Service (Germany). Chang-Liver cells were placed in a Petri dish containing Basal Medium Eagle (BME, Cat. No. B-9638, Sigma, Mo., USA) supplemented with 10% fetal bovine serum (FBS), 1.5 g/L $NaHCO_2$, 0.1 mM nonessential amino acids, 2.0 mM glutamine, 100 U/mL penicillin G, 100 μg/mL streptomycin, and 10 g/L phenol red, followed by cultivation in an incubator with culture conditions set at 37° C. and 5% $CO_2$. Medium change was performed every two days, approximately. When cell density reached about 80% confluence, medium was removed, followed by washing the cells two times with phosphate buffered saline (PBS). 1% trypsin-EDTA (Cat. No. 15400-054, GIBCO, USA) was added so as to detach the cells from the Petri dish. About one-fifth to one-tenth of the cells were transferred to anew Petri dish containing fresh BME medium, followed by cultivation in an incubator with culture conditions set at 37° C. and 5% $CO_2$.

2. HA22T, Human Hepatoma Cell Line:

HA22T (accession number: BCRC 60168) was purchased from Biosource Collection and Research Center (BCRC) belonging to Food Industry Research and Development Institute (FIRDI) (331 Shih-Pin Road, Hsinchu 300, Taiwan). HA22T cells were placed in a Petri dish containing Dulbecco's Modified Eagle's Medium (DMEM, Cat. No. D5523, Sigma, Mo., USA) supplemented with 10% FBS, 1.5 g/L $NaHCO_3$, 0.1 mM nonessential amino acids, 2.0 mM glutamine, 100 U/mL penicillin G, 100 μg/mL streptomycin, and 10 g/L phenol red, followed by cultivation in an incubator with culture conditions set at 37° C. and 5% $CO_2$. Medium change was performed every two days, approximately. When cell density reached about 80% confluence, medium was removed, followed by washing the cells two times with PBS. 1% trypsin-EDTA (Cat. No. 15400-054, GIBCO, USA) was added so as to detach the cells from the Petri dish. About one-fifth to one-tenth of the cells were transferred to a new Petri dish containing fresh DMEM medium, followed by cultivation in an incubator with culture conditions set at 37° C. and 5% $CO_2$.

General Experimental Procedures:
1. Preparation of Total Protein Sample:

The HA22T cells tested in a respective one of the following examples were washed twice using PBS, followed by adding 200 μL of lysis buffer [containing 50 mM Tris-base (pH 7.5), 0.5 MNaCl, 1 mM EDTA (pH 8), 1 mM β-mercaptoethanol, 1% NP40, 1% glycerol, and 5 mg/mL protease inhibitor] and mixing evenly. The resultant cell mixture was placed in a microcentrifuge tube. Subsequently, the microcentrifuge tube containing the cell mixture was placed on ice for 30 minutes with shaking every 5 minutes. Centrifugation at 4° C. and 12000 rpm was conducted for 10 minutes, followed by collecting supernatant serving as a total protein sample. The total protein sample was subjected to determination of protein concentration by virtue of Lowry protein assay.

2. Western Blotting:

SDS-PAGE was conducted using a vertical electrophoresis system (Mini PROTEAN® 3 Cell, Bio-Rad, USA). Two layers of polyacrylamide gels, i.e., a 12% separating gel and a 3.71% stacking gel, were prepared. 40 μg of the total protein sample, the nucleus protein sample, or the cytoplasmic protein sample prepared in a respective one of the following examples was loaded into a U-type well. SDS-PAGE was run at a constant voltage of 75 V using electrophoresis buffer (containing 0.3% Tris-base, 1.47% glycine, and 0.1% SDS) for 2.5 hours.

After SDS-PAGE was completed, the separated proteins were transferred from the separating gel onto a polyvinylidene difluoride (PVDF) membrane (pore size: 0.45 μm, IPVH00010, Millipore Corporation, MA, USA) using Mini Trans-Blot® Cell (Bio-Rad, USA). The transfer was run at 4° C. and a constant voltage of 100 V for 2 hours. The blotted PVDF membrane was acquired and was subjected to a blocking treatment at room temperature by virtue of 5% (w/v) skim milk [in TBS (150 mM NaCl, 10 mM Tris-base, 0.05% Tween-20)] for 1 hour, followed by washing with TBS three times (10 minutes for each time). The primary antibody [diluted 1000-fold with TBS (150 mM NaCl, 10 mM Tris-base, 0.05% Tween-20)] was added. After the mixture was left standing at 4° C. overnight, TBS was used to wash three times (10 minutes for each time). The secondary antibody [diluted 2000-fold with TBS (150 mM NaCl, 10 mM Tris-base, 0.05% Tween-20)] was added. After one-hour reaction at room temperature, TBS was employed to wash three times (10 minutes for each time). Chemiluminescence staining was performed using Western Blotting Luminal Reagent (Cat. No. sc-2048, Santa Cruz Biotechnology, CA, USA), and photographing was conducted by virtue of LAS-3000 imaging system (Fujifilm, Tokyo, Japan).

3. Statistical Analysis:

Statistical analysis was performed using statistical software, Sigma Plot. The experimental data were expressed as mean±SEM, and were analyzed via t-test so as to assess the difference between the test groups. Statistical significance is indicated by $p<0.05$.

Example 1

Preparation of Product Containing Extract from *Zanthoxylum avicennae* (Lam.) DC.

9.5 kg of the root of *Zanthoxylum avicennae* (Lam.) DC. purchased from a traditional market in Vietnam was washed with water and was peeled to obtain root skin. Subsequently, the thus obtained root skin of *Zanthoxylum avicennae* (Lam.) DC. (2.3 kg) was dried in an oven (40° C.). The dried root skin of *Zanthoxylum avicennae* (Lam.) DC. (900 g) was placed in a clay pot, and was heated with stirring while 100 mL of banana vinegar was sprayed into the clay pot (namely, a processing treatment was conducted). 850 g of the processed root skin of *Zanthoxylum avicennae* (Lam.) DC. was washed thrice using water, and was soaked in 8 L of 95% ethanol at room temperature, followed by mixing uniformly. The mixture was stirred every four hours. After two days, the mixture was subjected to filtration using gauze such that an ethanol-containing filtrate was obtained. 200 mL of banana vinegar was then added into the ethanol-containing filtrate so as to form an extract-containing solution.

The residue resulting from the filtration, i.e., the root skin of *Zanthoxylum avicennae* (Lam.) DC., was soaked in 5 L of 95% ethanol for two days with stirring every four hours, followed by filtration using gauze. An ethanol-containing filtrate was thus acquired, and 200 mL of banana vinegar was subsequently added into the ethanol-containing filtrate. The aforementioned step was repeated two additional times. The total extract-containing solutions thus obtained were combined. Decompress concentrating was conducted at 30° C. using Rotavapor R-114 (Büchi, USA) for two days while 10 mL of banana vinegar was added every other hour, followed by desiccation in an oven (40~45° C.). A product containing the extract from *Zanthoxylum avicennae* (Lam.) DC. (designated as PYBBE), which was in powder form, was formed, and was dissolved in sterile water such that a PYBBE stock solution having a PYBBE concentration of 10 mg/mL was prepared.

Example 2

HPLC Analysis of Product Containing Extract from *Zanthoxylum avicennae* (Lam.) DC.

HPLC (high performance liquid chromatography) was conducted for the product containing the extract from *Zanthoxylum avicennae* (Lam.) DC. (PYBBE), which was prepared according the above Example 1, so as to investigate the composition of the same.

The HPLC instruments are as follows: Agilent 1100 series liquid chromatography system (Agilent Technologies, Palo Alto, Calif., USA) equipped with an online degasser (G1379A), a binary pump (G1312A), and a UV-Vis variable multiwavelength detector (G1314A); and a column (Xterra RP1 LC, size: 250 mm×4.6 mm, Waters Corp., Milford, Mass., USA).

The operating conditions of HPLC are as follows. The UV-Vis variable multiwavelength detector was set at a wavelength of 254 nm. The mobile phase was deionized water/methanol (20:80, v/v), and the flow rate of the mobile phase was 0.7 mL/min. Gradient elution with the mobile phase was conducted for 60 minutes as follows: the deionized water was increased from 20% to 50% in 15 minutes, was increased from 50% to 70% in 25 minutes, and was maintained at 70% for 20 minutes.

HPLC was also conducted for the extract from the leaf of *Zanthoxylum avicennae* (Lam.) DC., which was prepared according to the method described in T. T. Thuy et al. (1999, supra), using the aforementioned equipments and operating conditions.

Results:

FIG. 1 is a HPLC elution profile of PYBBE prepared according to the above Example 1. As shown in FIG. 1, 13 peaks (respectively labeled a1, a2, a3, a4, a5, a6, a7, a8, a9, a10, a11, a12, and a13) can be found between a retention time of 0 minute and a retention time of 60 minutes.

Figure 2:
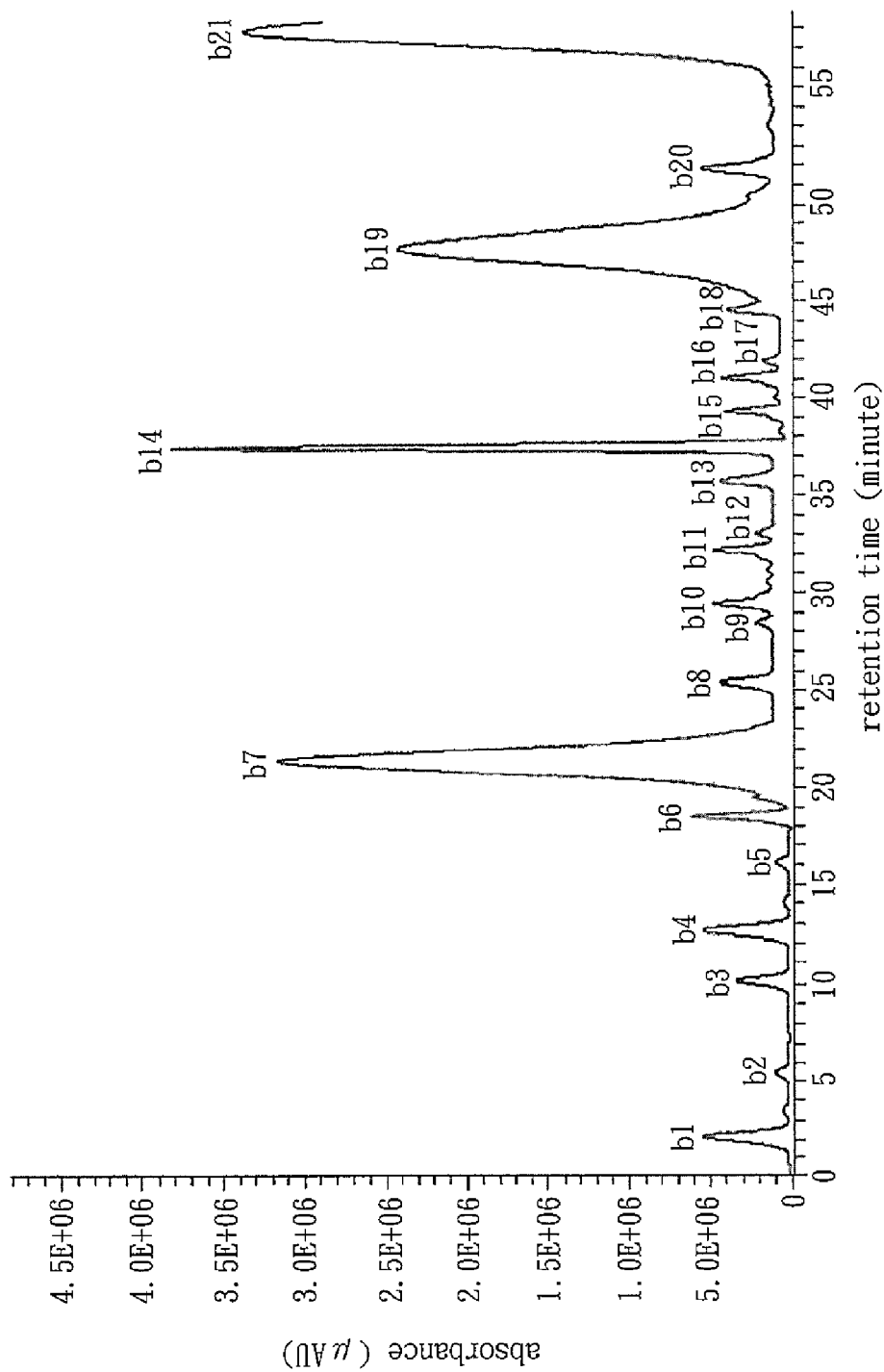
FIG. 2 is a HPLC elution profile belonging to the extract from the leaf of *Zanthoxylum avicennae* (Lam.) DC. prepared according to the method described in T. T. Thuy et al. (1999, supra)

FIG. 2 is a HPLC elution profile belonging to the extract from the leaf of *Zanthoxylum avicennae* (Lam.) DC. prepared according to the method described in T. T. Thuy et al. (1999, supra). As shown in FIG. 2, 21 peaks (respectively labeled b1, b2, b3, b4, b5, b6, b7, b8, b9, b10, b11, b12, b13, b14, b15, b16, b17, b18, b19, b20, and b21) can be observed between a retention time of 0 minute and a retention time of 60 minutes.

By virtue of the comparison between the positions of the peaks in FIGS. 1 and 2, it can be found that the composition of PYBBE of this invention is obviously different from the composition of the extract from the leaf of *Zanthoxylum avicennae* (Lam.) DC. prepared according to the method described in T. T. Thuy et al. (1999, supra).

Example 3

Cell Viability Analysis of PYBBE, and Effects of PYBBE on Cell Cycle and Proliferation of HA22T Cells In order to determine cytotoxicity of PYBBE according to this invention, and effects of PYBBE according to this invention on the cell cycle and proliferation of HA22T cells, PYBBE prepared according to the above Example 1 was used in the following experiments.

A. Cell Viability Analysis

HA22T cells were divided into 6 groups including a control group and five experimental groups (i.e., groups 1-5). Each group of HA22T cells was plated in a 24-well plate containing DMEM (supplemented with 10% FBS, 1.5 g/L NaHCO$_3$, 0.1 mM nonessential amino acids, 2.0 mM glutamine, 100 U/mL penicillin G, 100 µg/mL streptomycin, and 10 g/L phenol red) at a concentration of 2×10$^5$ cell/well, followed by cultivation in an incubator (37° C., 5% CO$_2$). When the cell density reached about 80% confluence, the old medium was replaced with fresh DMEM [supplemented with 1% cosmic calf serum (CCS), 1.5 g/L NaHCO$_3$, 0.2 mM nonessential amino acids, 2.0 mM glutamine, 100 U/mL penicillin G, and 100 µg/mL streptomycin], followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 µg/mL. The cells in each group were further cultivated for 24 hours.

Subsequently, the medium was removed, followed by washing twice with PBS. 500 µL of MTT/DMEM (v/v=1:9; MTT:thiazolyl blue tetrazolium bromide; DMEM was supplemented with 1% CCS, 1.5 g/L NaHCO$_3$, 0.2 mM nonessential amino acids, 2.0 mM glutamine, 100 U/mL penicillin G, and 100 µg/mL streptomycin) was added, followed by cultivation in an incubator (37° C., 5% CO$_2$) for 4 hours. 500 µL of isopropanol was then added, and the reaction was allowed to proceed for 10 minutes. 200 µL of the resultant mixture was placed in a 96-well plate. Absorbance at 570 nm (OD$_{570}$) was measured using a spectrophotometer (U-2001, Hitachi). Furthermore, Chang-Liver cells were also subjected to the aforementioned procedures except that BME was used instead of DMEM.

Relative cell viability percentage (%) can be calculated by substituting the absorbance into the following formula:

$$A=(B/C)\times 100 \qquad (1)$$

where
A=relative cell viability percentage
B=OD$_{570}$ of a respective one of the experimental groups and the control group
C=OD$_{570}$ of the control group The experimental data were analyzed according to the method as described in the section, entitled "3. Statistical analysis", of the General Experimental Procedures.

B. Expression Level of Protein Related to Cell Cycle Regulation

HA22T cells were divided into 6 groups including a control group and five experimental groups (i.e., groups 1-5). Each group of HA22T cells was placed in a Petri dish (diameter: 10 cm) containing DMEM (supplemented with 10% FBS, 1.5 g/L NaHCO$_3$, 0.1 mM nonessential amino acids, 2.0 mM glutamine, 100 U/mL penicillin G, 100 µg/mL streptomycin, and 10 g/L phenol red), followed by cultivation in an incubator (37° C., 5% CO$_2$). When the cell density reached about 80% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 µg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 µg/mL.

After HA22T cells in each group were cultivated in an incubator (37° C., 5% CO$_2$) for 24 hours, the total protein sample of each group was prepared according to the method as described in the section, entitled "1. Preparation of total protein sample", of the General Experimental Procedures. The total protein examples were subjected to a Western blotting experiment according to the method as described in the section, entitled "2. Western blotting", of the General Experimental Procedures so as to detect the following proteins: proliferating cell nuclear antigen (PCNA), cyclin A, cyclin D1, cyclin E, cyclin B1, p21, p27, p-p53, p53, c-Fos, c-Myc, and α-tubulin (serving as an internal control). The primary and secondary antibodies used for each protein are shown in Table 1.

Additionally, Chang-Liver cells were also subjected to the aforementioned procedures except that BME was used instead of DMEM, and that the total protein samples were subjected to a Western blotting experiment so as to detect PCNA and α-tubulin (serving as an internal control).

TABLE 1

Primary and secondary antibodies used in Western blotting experiment

| Protein | Primary antibody | Secondary antibody |
|---|---|---|
| PCNA | rabbit anti PCNA (FL-261) polyclonal antibody (Santa Cruz, USA, Cat. No. sc-7907) | goat anti-rabbit IgG-HRP antibody, Santa Cruz, USA, Cat. No. sc-2004) |
| cyclin A | rabbit anti cyclin A (H-432) polyclonal antibody (Santa Cruz, USA, Cat. No. sc-751) | goat anti-rabbit IgG-HRP antibody |
| cyclin D1 | mouse anti cyclin D1 (HD11) monoclonal antibody (Santa Cruz, USA, Cat. No. sc-246) | goat anti-mouse IgG-HRP antibody (Santa Cruz, USA, Cat. No. sc-2005) |
| cyclin E | mouse anti cyclin E (E-4) monoclonal antibody (Santa Cruz, USA, Cat. No. sc-25303) | goat anti-mouse IgG-HRP antibody |
| cyclin B1 | rabbit anti cyclin B1 (H-433) polyclonal antibody (Santa Cruz, USA, Cat. No. sc-752) | goat anti-rabbit IgG-HRP antibody |
| c-Fos | rabbit anti c-Fos (4) polyclonal antibody (Santa Cruz, USA, Cat. No. sc-52) | goat anti-rabbit IgG-HRP antibody |
| c-Myc | mouse anti c-Myc (C-33) monoclonal antibody (Santa Cruz, USA, Cat. No. sc-42) | goat anti-mouse IgG-HRP antibody |
| p21 | mouse anti p21 (F-5) monoclonal antibody (Santa Cruz, USA, Cat. No. sc-6246) | goat anti-mouse IgG-HRP antibody |
| P27 | mouse anti p27 (F-8) monoclonal antibody (Santa Cruz, USA, Cat. No. sc-1641) | goat anti-mouse IgG-HRP antibody |

TABLE 1-continued

Primary and secondary antibodies used
in Western blotting experiment

| Protein | Primary antibody | Secondary antibody |
| --- | --- | --- |
| p-p53 | goat anti p-p53 (Thr 377) polyclonal antibody (Santa Cruz, USA, Cat. No. sc-17274) | donkey anti-goat IgG-HRP antibody (Santa Cruz, USA, Cat. No. sc-2020) |
| P53 | goat anti p53 (C-19) polyclonal antibody (Santa Cruz, USA, Cat. No. sc-1311) | donkey anti-goat IgG-HRP antibody |
| α-tubulin | mouse anti α-tubulin (B-7) monoclonal antibody (Santa Cruz, USA, Cat. No. sc-5286) | goat anti-mouse IgG-HRP antibody |

C. Flow Cytometry

HA22T cells were divided into 6 groups including a control group and five experimental groups (i.e., groups 1-5). Each group of HA22T cells was plated in a Petri dish containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 80% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

HA22T cells in each group were cultivated in an incubator (37° C., 5% CO$_2$) for 24 hours. The medium was removed, followed by washing twice using PBS. 0.5 mL of 1% trypsin-EDTA was added to detach the cells from the Petri dish. Subsequently, 0.5 mL of DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin) was added, followed by centrifugation at 1500 rpm for 5 minutes. After supernatant was removed, 1 mL of PBS (4° C.) was added to suspend the cells. Centrifugation at 1500 rpm was conducted for 5 minutes, and supernatant was removed. 200 μL of PBS was added for cell suspension. 800 μL of absolute alcohol was added dropwise for cell fixation. The mixture was left standing at −20° C. for 1 hour, followed by centrifugation at 1500 rpm for 5 minutes. After supernatant was removed, 1 mL of Cyde Ntock/Triton X-100 (i.e., a staining solution containing 1% Triton X-100, 50 μg/mL RNase A, 400 μg/mL Cyde Ntock, and 55% PBS) was added. The resultant mixture was kept at room temperature and away from light for 30 minutes. Flow cytometry was performed using BD FACSCanto™ flow cytometer (BD Bioscienses, USA). Specifically, 10000 cells were analyzed each time. The cells were excited by Argon-ion laser beam of 488 nm and emitted fluorescence. The obtained data were subjected to cell cycle analysis using ModFit LT software and were subjected to statistical analysis according to the method as described in the section, entitled "3. Statistical analysis", of the General Experimental Procedures.

D. Wound Healing Assay

HA22T cells were divided into 6 groups including a control group and five experimental groups (i.e., groups 1-5). Each group of HA22T cells was placed in a Petri dish (diameter: 10 cm) containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 80% confluence, a pipette tip was used to scratch the HA22T cells along a diameter of the Petri dish. Therefore, a gap along the diameter of the Petri dish was formed and had no cells attached thereto. The medium was removed, followed by washing twice with PBS. Fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin) was added, and cultivation was conducted for 4 hours. Subsequently, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% CO$_2$) for 48 hours, the medium was removed, followed by washing twice with PBS. Cells in the gap were observed and counted using an inverted microscope (CKX41, Olympus, Japan). Relative cell proliferation percentage (%) was calculated by substituting the number of cells into the following formula:

$$D=(E/F)\times 100 \qquad (2)$$

where

D=relative cell proliferation percentage

E=number of cells in the gap regarding a respective one of the experimental groups and the control group F=number of cells in the gap regarding the control group The experimental data were analyzed according to the method as described in the section, entitled "3. Statistical analysis", of the General Experimental Procedures.

Figure 3A:
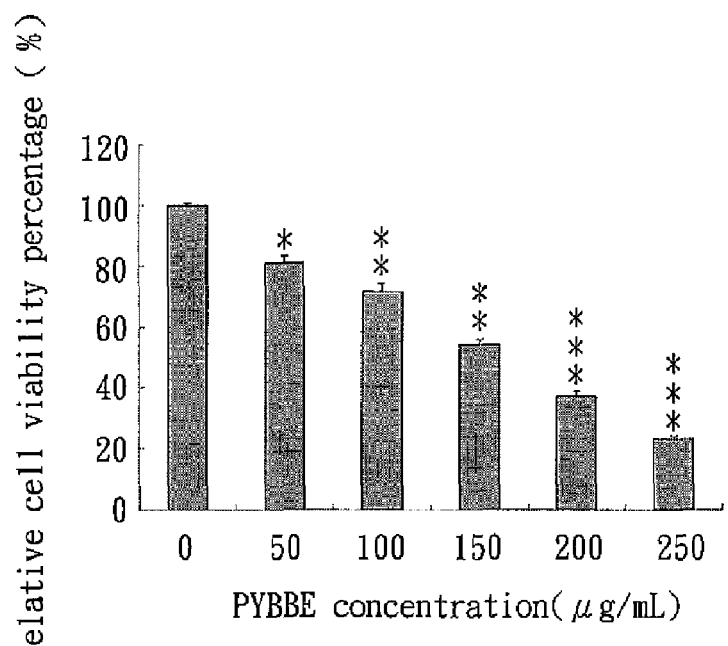
FIGS. 3(A) and 3(B) respectively show the relative cell viability percentage of HA22T and Chang-Liver cells treated with different concentrations of PYBBE, in which the relative cell viability percentage is expressed as mean±SEM; and the symbols "*", "* *", and "* * *" respectively represent $p<0.05$, $p<0.01$, and $p<0.001$.
Figure 3B:
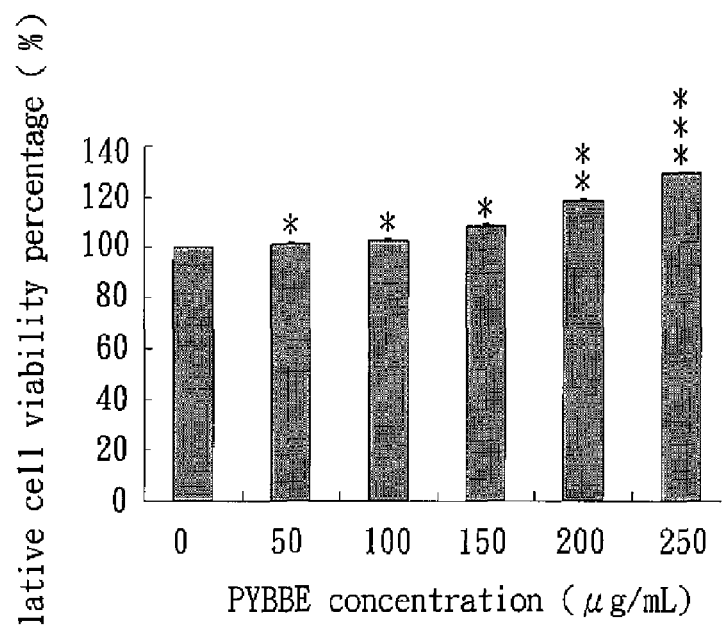

Results:

FIGS. 3(A) and 3(B) respectively show the relative cell viability percentages of HA22T and Chang-Liver cells treated with different concentrations of PYBBE. As shown in FIG. 3 (A), the relative cell viability percentage of HA22T cells in each of groups 1-5 is significantly lower than that of HA22T cells in the control group. In particular, the relative cell viability percentage of HA22T cells in group 5 is the lowest (i.e., about 23.45%). Moreover, as shown in FIG. 3(B), the relative cell viability percentage of Chang-Liver cells in each of groups 1-5 is significantly higher than that of Chang-Liver cells in the control group. Particularly, the relative cell viability percentage of Chang-Liver cells in group 5 is the highest (i.e., about 129.55%). The experimental results of section A of Example 3 reveal that the product containing the extract from *Zanthoxylum avicennae* (Lam.) DC. is cytotoxic to the hepatoma cells, but the same is harmless to the normal liver cells.

Figure 4:
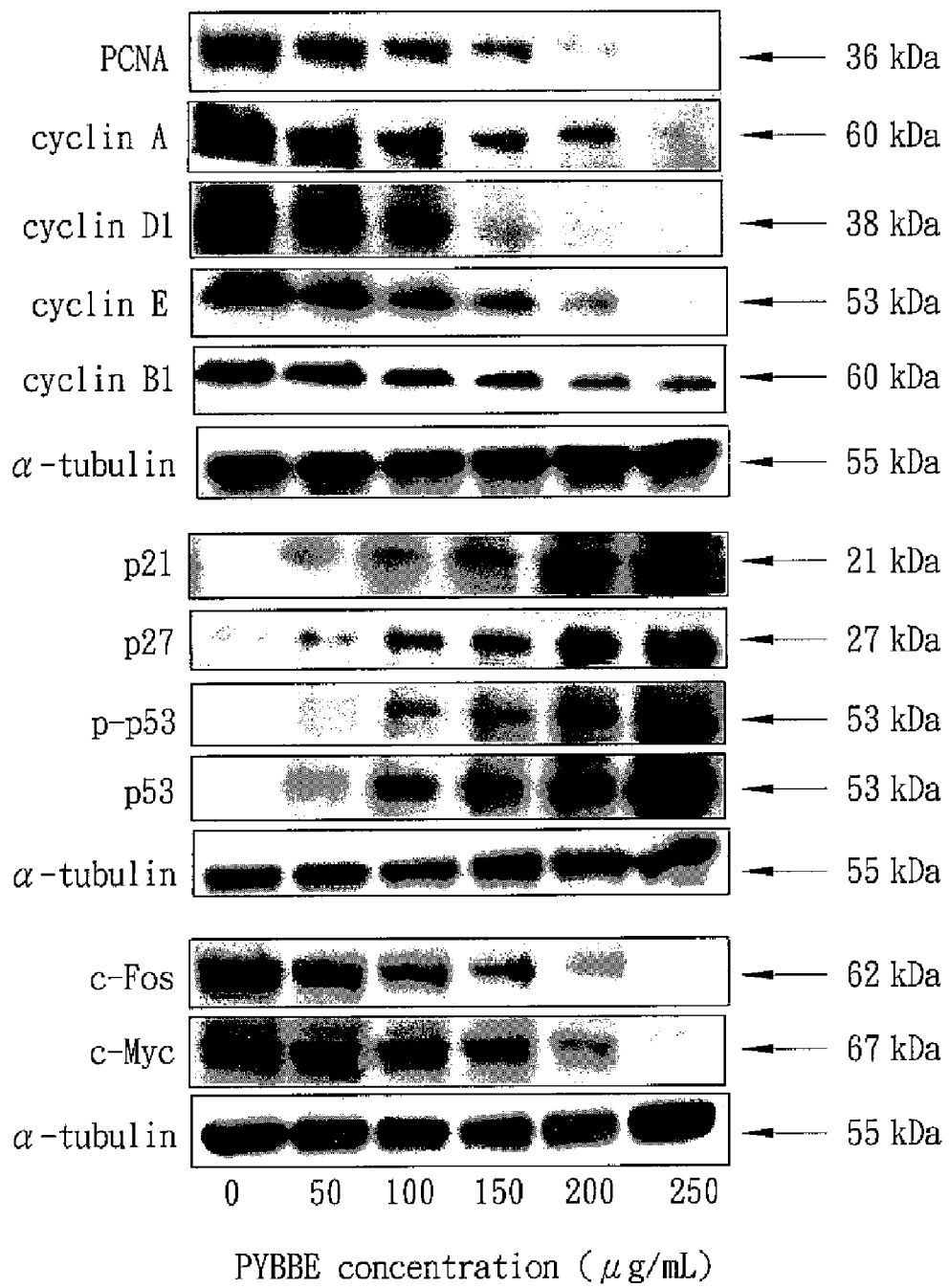
FIG. 4 is a Western blot showing the expression levels of PCNA, cyclin A, cyclin D1, cyclin E, cyclin B1, p21, p27, p-p53, p53, c-Fos, and c-Myc in HA22T cells treated with different concentrations of PYBBE.

FIG. 4 is a Western blot showing the expression levels of PCNA, cyclin A, cyclin D1, cyclin E, cyclin B1, p21, p27, p-p53, p53, c-Fos, and c-Myc in HA22T cells treated with different concentrations of PYBBE. As shown in FIG. 4, the expression levels of PCNA, cyclin A, cyclin D1, cyclin E, cyclin B1, c-Fos, and c-Myc in HA22T cells of each of groups 1-5 are lower than those in HA22T cells of the control group, and the expression levels of PCNA, cyclin A, cyclin D1, cyclin E, cyclin B1, c-Fos, and c-Myc decrease when PYBBE concentration increases. Additionally, the expression levels of p21, p27, p-p53, and p53 in HA22T cells of each of groups 1-5 are higher than those in HA22T cells of the control group, and the expression levels of p21, p27, p-p53, and p53 increase when PYBBE concentration increases.

Figure 5:
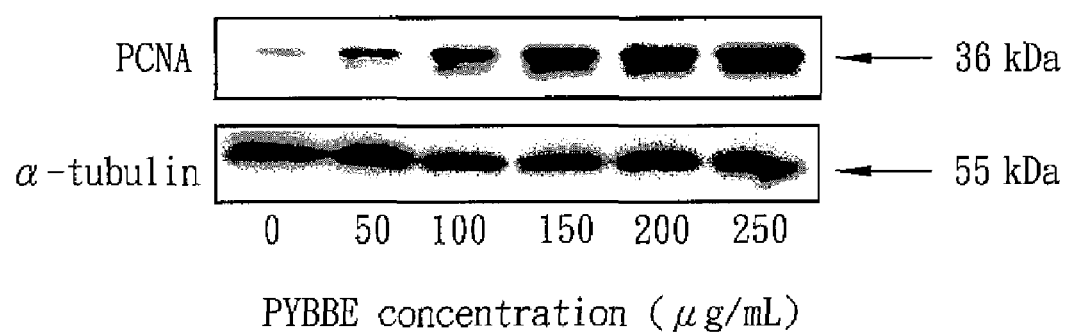
FIG. 5 is a Western blot showing the expression level of PCNA in Chang-Liver cells treated with different concentrations of PYBBE.

FIG. 5 is a Western blot showing the expression level of PCNA in Chang-Liver cells treated with different concentrations of PYBBE. As shown in FIG. 5, the expression level of PCNA in Chang-Liver cells of each of groups 1-5 is higher than that in Chang-Liver cells of the control group, and the expression level of PCNA increases when PYBBE concentration increases.

Accordingly, the experimental results of section B of Example 3 manifest that: there are positive dose-effect relationships between the dose of PYBBE and the effect of decreasing the expression levels of PCNA, cyclin A, cyclin D1, cyclin E, cyclin B1, c-Fos, and c-Myc in hepatoma cells, and between the dose of PYBBE and the effect of increasing the expression levels of p21, p27, p-p53, and p53 in hepatoma cells; and there is also a positive dose-effect relationship between the dose of PYBBE and the effect of increasing the expression level of PCNA in normal liver cells. Consequently, the applicants preliminarily infer that: PYBBE of this invention is able to inhibit cell cycle progression by regulating the expression of the proteins related to cell cycle regulation in hepatoma cells, thereby being capable of inhibiting proliferation of HA22T cells; and PYBBE of this invention is able to sufficiently enhance the expression of PCNA in normal liver cells, thereby being effective in facilitating proliferation of normal liver cells.

Figure 6:
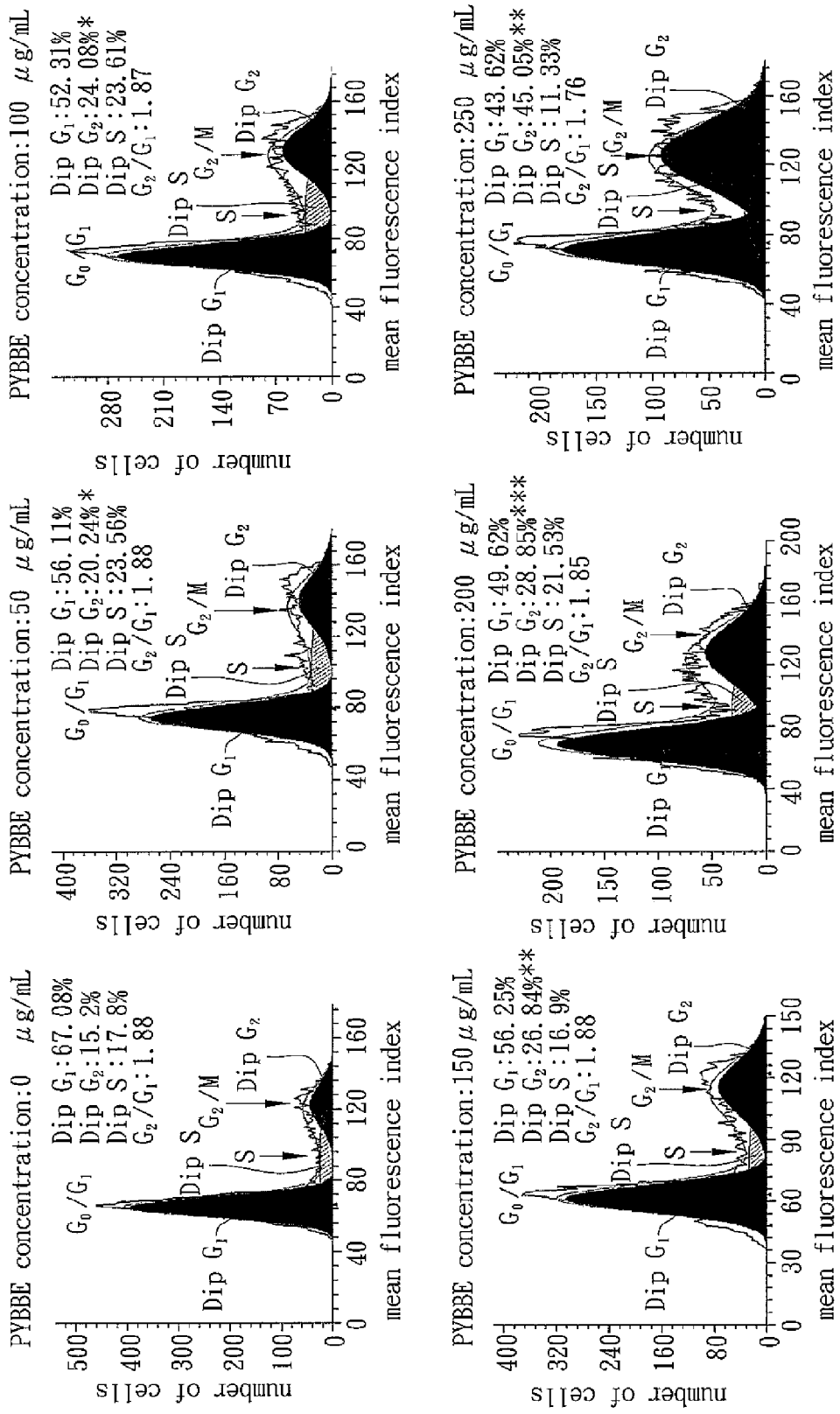
FIG. 6 shows the cell cycle status of HA22T cells treated with different concentrations of PYBBE, in which the symbols "*", "", and "*" respectively represent $p<0.05$, $p<0.01$, $p<0.001$.

FIG. 6 shows the cell cycle status of HA22T cells treated with different concentrations of PYBBE. As shown in FIG. 6, the number of HA22T cells in $G_2/M$ phase with respect to each of groups 1-5 is higher than that with respect to the control group, and the number of HA22T cells in $G_2/M$ phase increases when PYBBE concentration increases. The experimental results of section C of Example 3 indicate that: there is a positive dose-effect relationship between the dose of PYBBE and the effect of inducing cell cycle arrest. Thus, the applicants preliminarily infer that: PYBBE of this invention is able to arrest HA22T cells in $G_2/M$ phase of the cell cycle, thereby being effective in inhibiting proliferation of HA22T cells.

Figure 7:
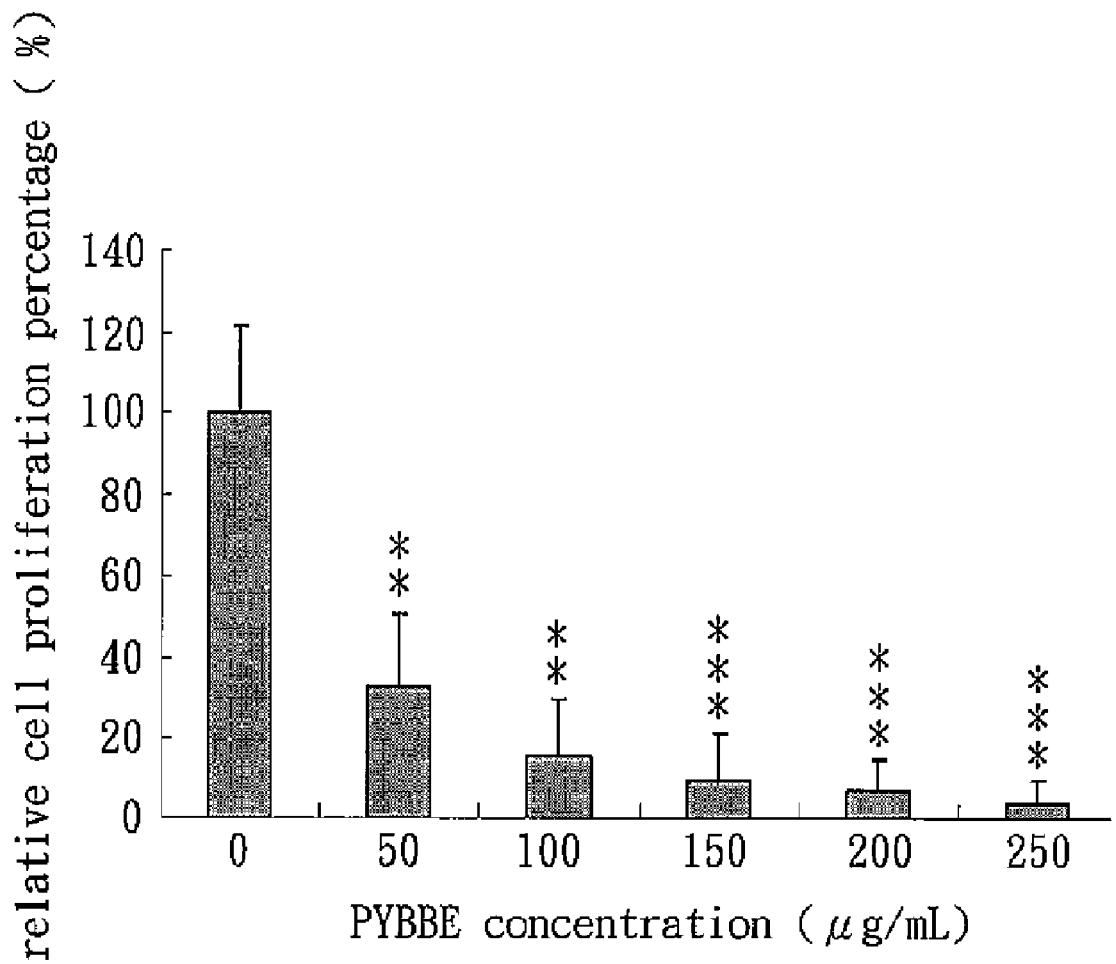
FIG. 7 shows the relative cell proliferation percentage of HA22T cells treated with different concentrations of PYBBE, in which the relative cell proliferation percentage is expressed as mean±SEM; and the symbols "**" and "* * *" respectively represent $p<0.01$ and $p<0.001$.

FIG. 7 shows the relative cell proliferation percentage of HA22T cells treated with different concentrations of PYBBE. As shown in FIG. 7, the relative cell proliferation percentage of HA22T cells in each of groups 1-5 is significantly lower than that of HA22T cells in the control group. In particular, the relative cell proliferation percentage of HA22T cells in group 5 is the lowest (i.e., 4.1%). The experimental results of section D of Example 3 reveal that there is a positive dose-effect relationship between the dose of PYBBE and the effect of inhibiting proliferation of HA22T cells.

Example 4

Effect of Product Containing Extract from
*Zanthoxylum avicennae* (Lam.) DC. on Apoptosis of HA22T Cells In order to evaluate the effect of PYBBE according to this invention on induction of apoptosis of HA22T cells, PYBBE obtained in the above Example 1 was subjected to TUNEL (terminal deoxynucleotidyl transferase mediated dUTP nick end labeling) assay.

HA22T cells were divided into 6 groups including a control group and five experimental groups (i.e., groups 1-5). Each group of HA22T cells was plated in a 24-well plate containing DMEM (supplemented with 10% FBS, 1.5 g/L $NaHCO_3$, 0.1 mM nonessential amino acids, 2.0 mM glutamine, 100 U/mL penicillin G, 100 μg/mL streptomycin, and 10 g/L phenol red) at a concentration of $2 \times 10^5$ cell/well, followed by cultivation in an incubator (37° C., 5% $CO_2$). When the cell density reached about 80% confluence, the old medium was replaced with fresh DMEM (supplemented with 1% CCS, 1.5 g/L $NaHCO_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% $CO_2$) for 24 hours, TUNEL staining was conducted using In Situ Cell Death Detection Kit, Fluorescein (Roche, Germany). First, the liquid in each well was removed, followed by washing three times with 500 μL of PBS. 300 μL of the fixation solution [4% paraformaldehyde in PBS (pH 7.4)] was added at room temperature, and the fixation reaction was then allowed to proceed for 1 hour. Paraformaldehyde was removed by washing five times with 500 μl of PBS. 300 μl of the permeabilization solution (0.1% Triton X-100 in 0.1% sodium citrate) was added at 4° C., and the reaction was allowed to proceed for 2 minutes, followed by washing five times with 500 μl of PBS. Subsequently, 1 μg/ml 4',6-diamidino-2-phenylindole (DAPI, diluted 10000-fold with PBS) was added. The mixture was kept at room temperature and away from light for 30 minutes, followed by washing five times with 500 μL of PBS. A TUNEL reaction mixture containing terminal deoxynucleotidyl transferase and fluorescein (i.e., a labeling dye) was added. The mixture was kept at 37° C. and away from light for 2 hours, followed by washing five times with PBS. The cells in the 24-well plate were observed using the excitation light (488 nm) for fluorescein and the excitation light (400 nm) for DAPI under an inverted microscope (CKX41, Olympus, Japan). The TUNEL stained (i.e., TUNEL positive) cells are the apoptotic cells. DAPI was used for counterstaining, and total cells counterstained with DAPI are blue. The number of TUNEL stained cells and the number of DAPI stained cells were quantified using ImageJ software. The apoptosis percentage (%) of HA22T cells in each group was calculated by substituting the number of cells into the following formula:

$$G=(H/I) \times 100 \qquad (3)$$

where
G=apoptosis percentage
H=number of TUNEL stained cells
I=number of DAPI stained cells The experimental data were analyzed according to the method as described in the section, entitled "3. Statistical analysis", of the General Experimental Procedures.

Figure 8:
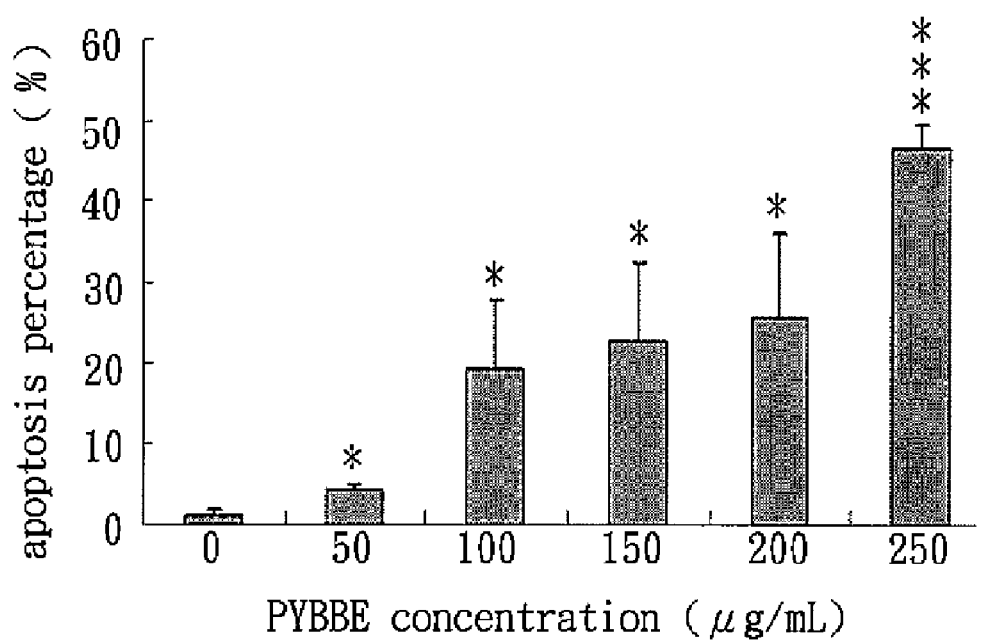
FIG. 8 shows the apoptosis percentage of HA22T cells treated with different concentrations of PYBBE, in which the apoptosis percentage is expressed as mean±SEM; and the symbols "*" and "* * *" respectively represent $p<0.05$ and $p<0.001$.

Results:

FIG. 8 shows the apoptosis percentage of HA22T cells treated with different concentrations of PYBBE. As shown in FIG. 8, the apoptosis percentage of HA22T cells in each of groups 1-5 is significantly higher than that of HA22T cells in the control group. Particularly, the apoptosis percentage of HA22T cells in group 5 is the highest (i.e., 46.66%). The aforementioned experimental results manifest that there is a positive dose-effect relationship between the dose of PYBBE and the effect of inducing apoptosis of HA22T cells.

Example 5

Effect of Product Containing Extract from
*Zanthoxylum avicennae* (Lam.) DC. on Apoptosis Signal Transduction Pathway in HA22T Cells In order to investigate the effects of PYBBE according to this invention on the death receptor-dependent apoptosis signal transduction pathway in HA22T cells, on the mitochondrial membrane potential in HA22T cells, and on the mitochondria-dependent apoptosis signal transduction pathway in HA22T cells, the following experiments were performed.

A. Expression Level of Protein Related to Death Receptor-Dependent Apoptosis Signal Transduction Pathway This experiment was conducted generally according to the method as described in the section, entitled "B. Expression level of protein related to cell cycle regulation", of the above Example 3, except that a Western blotting experiment using the primary and secondary antibodies as shown in Table 2 was performed to detect the following proteins: FAS, FAS-L, FADD, TNFα, TNF-R1, caspase-8, t-BID, BID, and caspase-3.

TABLE 2

Primary and secondary antibodies used in Western blotting experiment

| Protein | Primary antibody | Secondary antibody |
| --- | --- | --- |
| FAS | rabbit anti FAS (FL-335) polyclonal antibody (Santa Cruz, USA, Cat. No. sc-7886) | goat anti-rabbit IgG-HRP antibody |
| FAS-L | rabbit anti FAS-L (Q-20) polyclonal antibody (Santa Cruz, USA, Cat. No. sc-956) | goat anti-rabbit IgG-HRP antibody |
| FADD | goat anti FADD (S-18) polyclonal antibody (Santa Cruz, USA, Cat. No. sc-6035) | donkey anti-goat IgG-HRP antibody |
| TNFα | goat anti TNFα (N-19) polyclonal antibody (Santa Cruz, USA, Cat. No. sc-1350) | donkey anti-goat IgG-HRP antibody |
| TNF-R1 | goat anti TNF-R1 (E-20) polyclonal antibody (Santa Cruz, USA, Cat. No. sc-1070) | donkey anti-goat IgG-HRP antibody |
| caspase-8 | goat anti caspase-8 p18 (T-16) polyclonal antibody (Santa Cruz, USA, Cat. No. sc-6134) | donkey anti-goat IgG-HRP antibody |
| t-BID | rabbit anti BID (FL-195) polyclonal antibody (Santa Cruz, Cat. No. sc-11423) | goat anti-rabbit IgG-HRP antibody |
| BID | rabbit anti BID (FL-195) polyclonal antibody (Santa Cruz, Cat. No. sc-11423) | goat anti-rabbit IgG-HRP antibody |
| caspase-3 | rabbit anti caspase-3 (H-277) polyclonal antibody (Santa Cruz, Cat. No. sc-7148) | goat anti-rabbit IgG-HRP antibody |
| α-tubulin | mouse anti α-tubulin (B-7) monoclonal antibody (Santa Cruz, USA, Cat. No. sc-5286) | goat anti-mouse IgG-HRP antibody |

B. Mitochondrial Membrane Potential Assay

It is known that depolarization of the mitochondrial membrane potential is an early mark event in apoptosis. Consequently, in order to examine whether PYBBE of this invention is able to affect mitochondrial membrane potential in HA22T cells for further inducing apoptosis of HA22T cells, the following experiments were conducted.

HA22T cells were divided into 6 groups including a control group and five experimental groups (i.e., groups 1-5). Each group of HA22T cells was placed in a Petri dish (diameter: 4 cm) containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 50% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% CO$_2$) for 24 hours, staining was performed using Mitochondria Staining Kit (Sigma-aldrich, Cat. No. CS0390, MO, USA) according to the manufacturer's instructions. The liquid in each well was removed, followed by washing three times with 1 mL of PBS. 1 mL of staining solution [containing 2.5 μg/mL JC-1, 0.5×JC-1 staining buffer, and 50% DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin)] was added at room temperature, and the reaction was allowed to proceed in an incubator (37° C., 5% CO$_2$) for 20 minutes. The staining solution was removed, followed by washing thrice with 0.2×JC-1 staining buffer. 3 mL of DMEM (supplemented with 10% FBS, 1.5 g/L NaHCO$_3$, 0.1 mM nonessential amino acids, 2.0 mM glutamine, 100 U/mL penicillin G, and 100 μg/mL streptomycin) was then added. Under a laser scanning spectral confocal microscope (Leica TCS SP2, Germany), red and green fluorescence were respectively observed using the excitation light of 577 nm and the excitation light of 488 nm. The mitochondrial membrane potential in the cells emitting red fluorescence was normal, and the mitochondrial membrane potential in the cells emitting green fluorescence was depolarized.

C. Expression Level of Protein Related to Mitochondria-Dependent Apoptosis Signal Transduction Pathway This experiment was conducted generally according to the method as described in the section, entitled "B. Expression level of protein related to cell cycle regulation", of the above Example 3, except that a Western blotting experiment using the primary and secondary antibodies as shown in Table 3 was performed to detect the following proteins: Bax, Bak, p-Bad, Bad, Bcl-2, Bcl-x$_L$, BID, t-BID, cytochrome c, caspase-9, caspase-3, and AIF.

TABLE 3

Primary and secondary antibodies used in Western blotting experiment

| Protein | Primary antibody | Secondary antibody |
| --- | --- | --- |
| Bax | rabbit anti Bax (P-19) polyclonal antibody (Santa Cruz, USA, Cat. No. sc-526) | goat anti-rabbit IgG-HRP antibody |
| Bak | rabbit anti Bak (H-211) polyclonal antibody (Santa Cruz, USA, Cat. No. sc-7873) | goat anti-rabbit IgG-HRP antibody |
| p-Bad | rabbit anti phospho-Bad (Ser 136) polyclonal antibody (Cell Signaling, USA, Cat. No. 9295) | goat anti-rabbit IgG-HRP antibody |

TABLE 3-continued

Primary and secondary antibodies used in Western blotting experiment

| Protein | Primary antibody | Secondary antibody |
| --- | --- | --- |
| Bad | mouse anti Bad monoclonal antibody (BD Biosciences, USA, Cat. No. 610391) | goat anti-mouse IgG-HRP antibody |
| Bcl-2 | mouse anti Bcl-2 monoclonal antibody (BD Biosciences, USA, Cat. No. 610539) | goat anti-mouse IgG-HRP antibody |
| Bcl-$x_L$ | mouse anti Bcl-$x_L$ (H-5) monoclonal antibody (Santa Cruz, Cat. No. sc-8392) | goat anti-mouse IgG-HRP antibody |
| BID | rabbit anti BID (FL-195) polyclonal antibody (Santa Cruz, Cat. No. sc-11423) | goat anti-rabbit IgG-HRP antibody |
| t-BID | rabbit anti BID (FL-195) polyclonal antibody (Santa Cruz, Cat. No. sc-11423) | goat anti-rabbit IgG-HRP antibody |
| cytochrome c | mouse anti cytochrome c (7H8) monoclonal antibody (Santa Cruz, Cat. No. sc-13560) | goat anti-mouse IgG-HRP antibody |
| caspase-9 | rabbit anti caspase-9 (H-170) polyclonal antibody (Santa Cruz, Cat. No. Sc-8355) | goat anti-rabbit IgG-HRP antibody |
| caspase-3 | rabbit anti caspase-3 (H-277) polyclonal antibody (Santa Cruz, Cat. No. Sc-7148) | goat anti-rabbit IgG-HRP antibody |
| AIF | mouse anti AIF (E-1) monoclonal antibody (Santa Cruz, Cat. No. sc-13116) | goat anti-mouse IgG-HRP antibody |
| α-tubulin | mouse anti α-tubulin (B-7) monoclonal antibody (Santa Cruz, USA, Cat. No. sc-5286) | goat anti-mouse IgG-HRP antibody |

Figure 9:
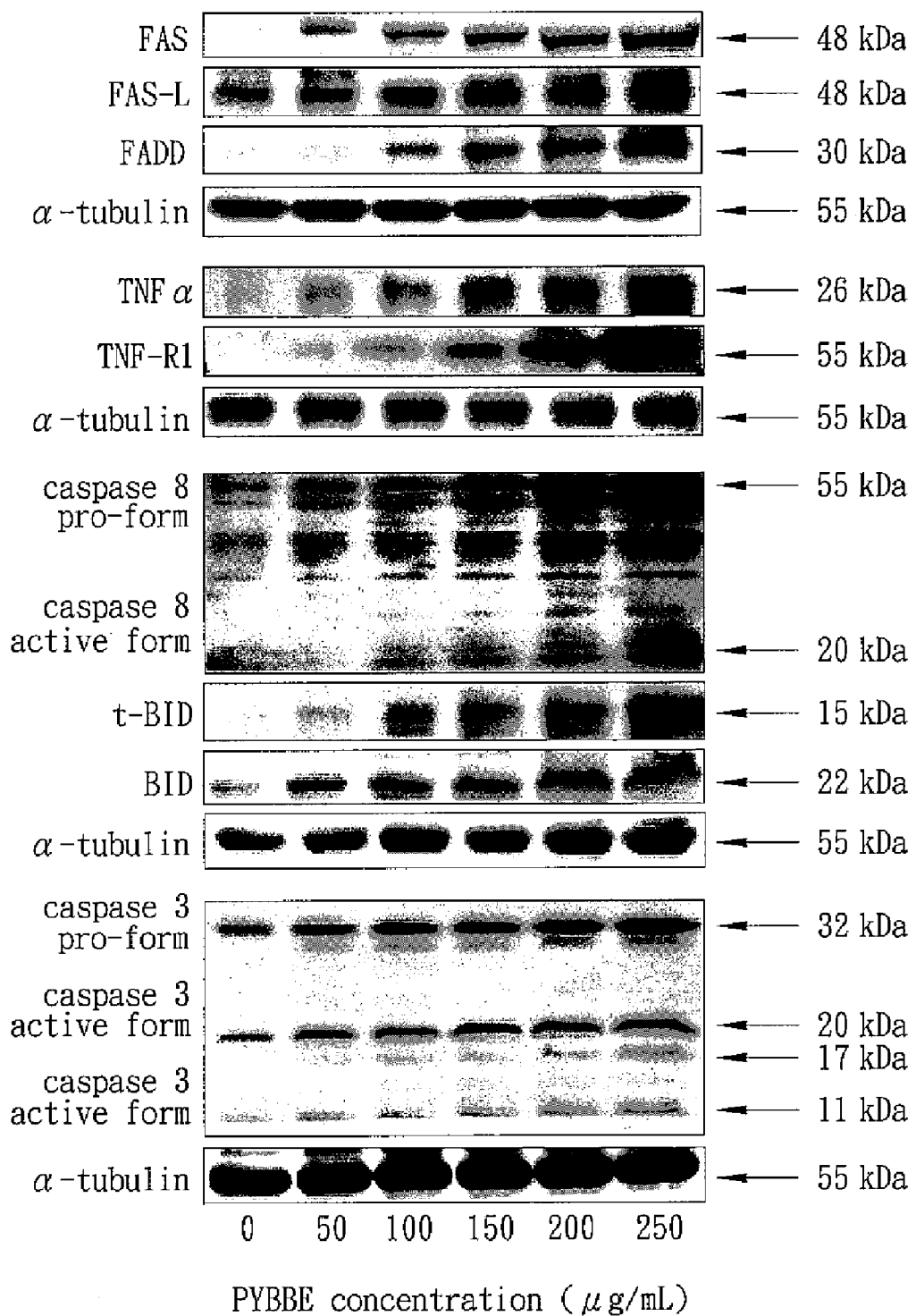
FIG. 9 is a Western blot showing the expression levels of FAS, FAS-L, FADD, INFα, TNF-R1, caspase-8 (the pro-form and the active form), t-BID, BID, and caspase-3 (the pro-form and the two active forms) in HA22T cells treated with different concentrations of PYBBE.

Results:

FIG. 9 is a Western blot showing the expression levels of FAS, FAS-L, FADD, INFα, TNF-R1, caspase-8 (the pro-form and the active form), t-BID, BID, and caspase-3 (the pro-form and the two active forms) in HA22T cells treated with different concentrations of PYBBE. As shown in FIG. 9, the expression levels of FAS, FAS-L, FADD, INFα, TNF-R1, caspase-8 (the pro-form and the active form), t-BID, BID, and caspase-3 (the pro-form and the two active forms) in HA22T cells of each of groups 1-5 are higher than those in HA22T cells of the control group. Therefore, the apppicants deduce that: PYBBE of this invention is able to sufficiently enhance the expression of FAS, FAS-L, FADD, TNFα, TNF-R1, caspase-8 (the pro-form and the active form), t-BID, BID, and caspase-3 (the pro-form and the two active forms), and to further activate the death receptor-dependent apoptosis signal transduction pathway, thereby being effective in inducing apoptosis of HA22T cells.

Figure 10:
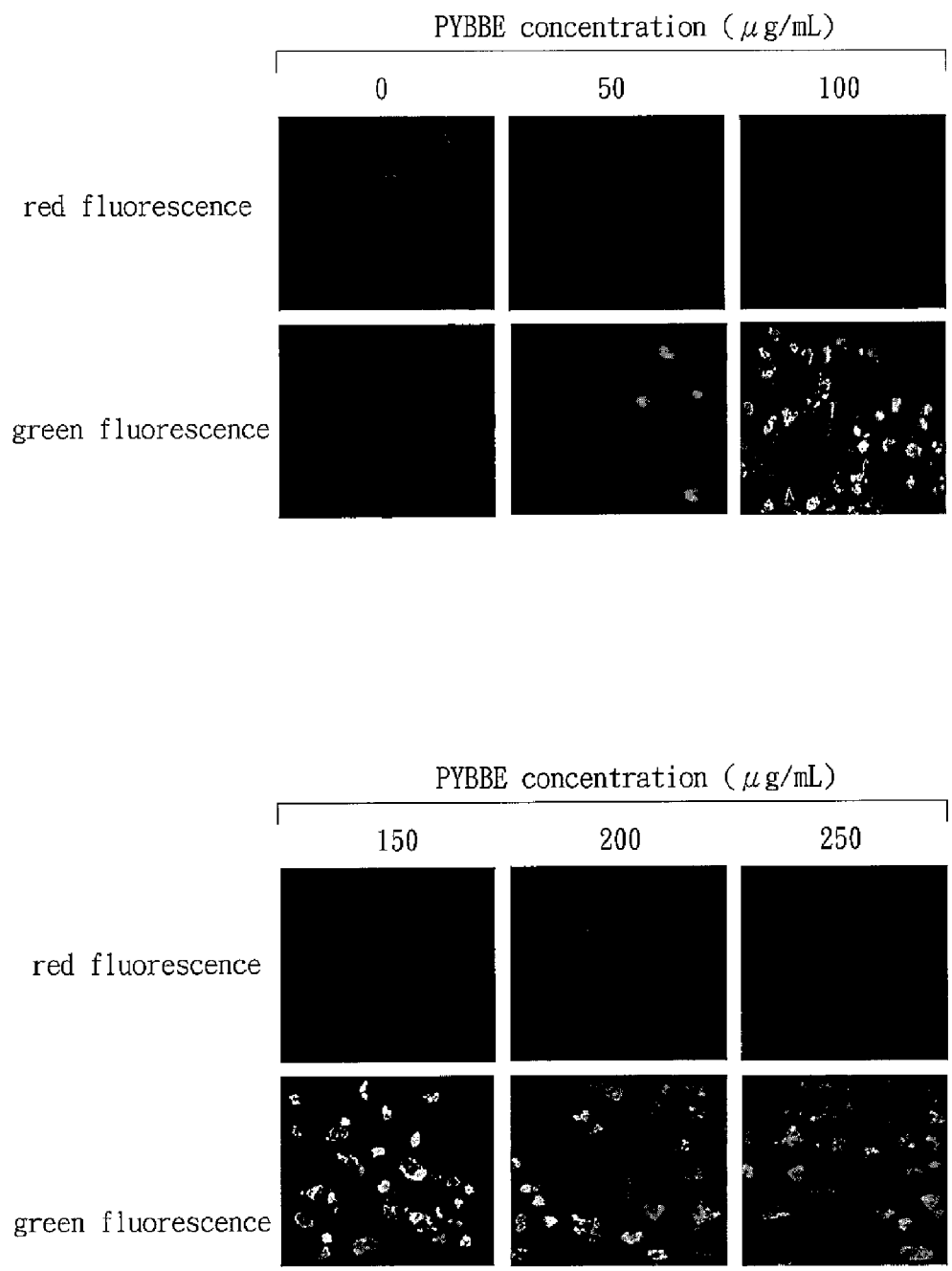
FIG. 10 shows the photomicrographs regarding the JC-1 staining results of HA22T cells treated with different concentrations of PYBBE.

FIG. 10 shows the photomicrographs regarding the JC-1 staining results of HA22T cells treated with different concentrations of PYBBE. As shown in FIG. 10, the degree of the depolarization of mitochondrial membrane potential in HA22T cells of each of groups 1-5 is higher than that in HA22T cells of the control group, and the degree of the depolarization of mitochondrial membrane potential increases when PYBBE concentration increases. The experimental results of section B of Example 5 indicate that: there is a positive dose-effect relationship between the dose of PYBBE and the effect of inducing the depolarization of mitochondrial membrane potential in HA22T cells. The applicants hence preliminarily presume that: PYBBE of this invention is capable of sufficiently depolarizing the mitochondrial membrane potential, thereby being able to induce apoptosis.

Figure 11:
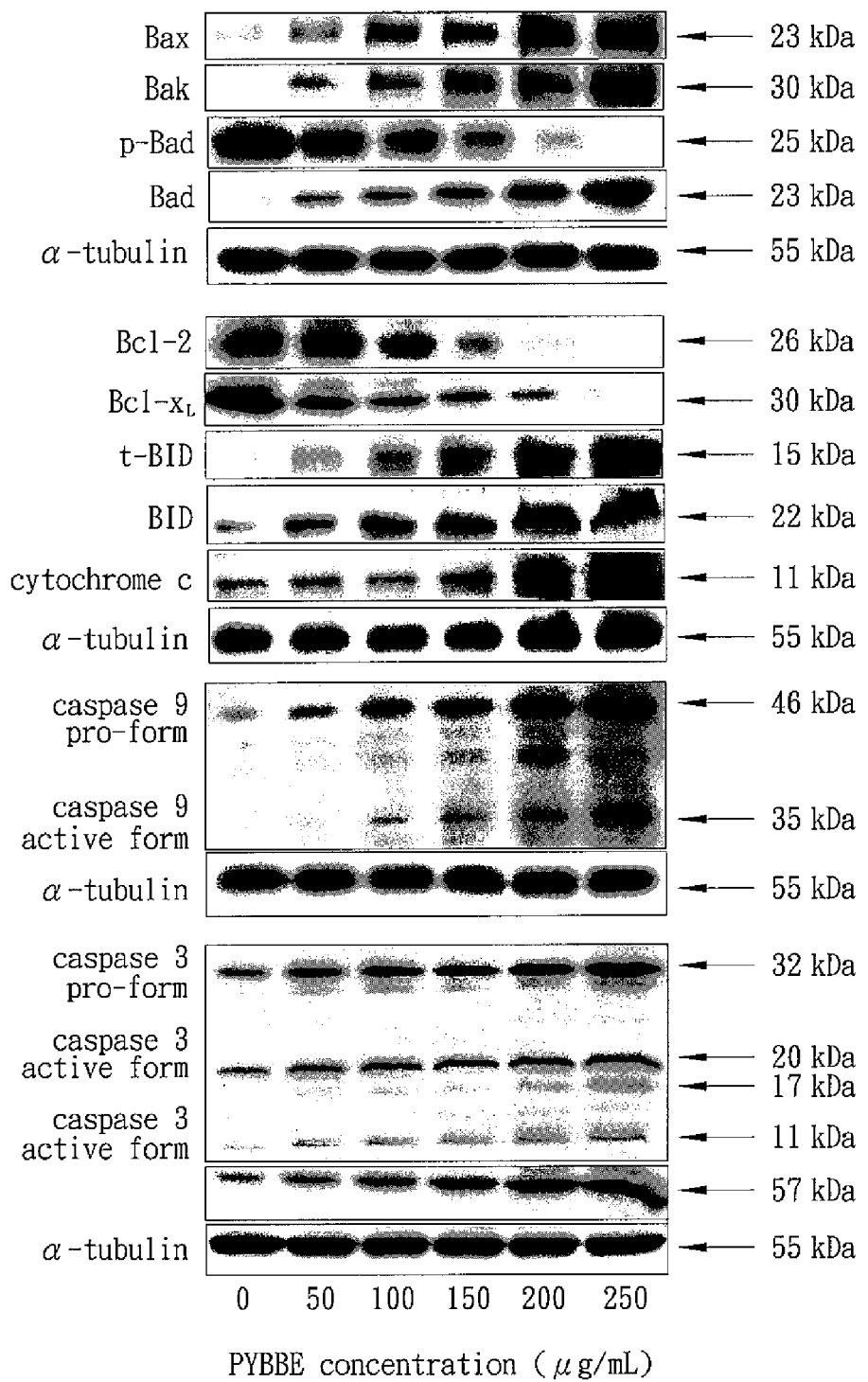
FIG. 11 is a Western blot showing the expression levels of Bax, Bak, p-Bad, Bad, Bcl-2, Bcl-$x_L$, t-BID, BID, cytochrome c, caspase-9 (the pro-form and the active form), caspase-3 (the pro-form and the two active forms), and AIF in HA22T cells treated with different concentrations of PYBBE.

FIG. 11 is a Western blot showing the expression levels of Bax, Bak, p-Bad, Bad, Bcl-2, Bcl-$x_L$, t-BID, BID, cytochrome c, caspase-9 (the pro-form and the active form), caspase-3 (the pro-form and the two active forms), and AIF in HA22T cells treated with different concentrations of PYBBE. As shown in FIG. 11, the expression levels of Bax, Bak, Bad, t-BID, BID, cytochrome c, caspase-9 (the pro-form and the active form), caspase-3 (the pro-form and the two active forms), and AIF in HA22T cells of each of groups 1-5 are higher than those in HA22T cells of the control group, and the expression levels of Bax, Bak, Bad, t-BID, BID, cytochrome c, caspase-9 (the pro-form and the active form), caspase-3 (the pro-form and the two active forms), and AIF increase when PYBBE concentraion increases. In addition, the expression levels of p-Bad, Bcl-2, and Bcl-$x_L$ in HA22T cells of each of groups 1-5 are lower than those in HA22T cells of the control group, and the expression levels of p-Bad, Bcl-2, Bcl-$x_L$ decrease when PYBBE concentration increases. The experimental results of section C of Example 5 reveal that: there are positive dose-effect relationships between the dose of PYBBE and the effect of enhancing the expression levels of Bax, Bak, Bad, t-BID, BID, cytochrome c, caspase-9 (the pro-form and the active form), caspase-3 (the pro-form and the two active forms), and AIF, and between the dose of PYBBE and the effect of reducing the expression levels of p-Bad, Bcl-2, and Bcl-$x_L$. Thus, the applicants preliminarily presume that: PYBBE of this invention is able to sufficiently enhance the expression of Bax, Bak, Bad, t-BID, BID, cytochrome c, caspase-9 (the pro-form and the active form), caspase-3 (the pro-form and the two active forms), and AIF, and to sufficiently reduce the expression of p-Bad, Bcl-2, and Bcl-$x_L$, thereby being further capable of activating the mitochondria-dependent apoptosis signal transduction pathway so as to induce apoptosis of HA22T cells.

Example 6

Effect of Product Containing Extract from *Zanthoxylum avicennae* (Lam.) DC. on Cell Survival Signal Transduction Pathway in HA22T Cells In order to investigate the effect of PYBBE according to this invention on the cell survival signal transduction pathway in HA22T cells, this experiment was conducted generally according to the method as described in the section, entitled "B. Expression level of protein related to cell cycle regulation", of the above Example 3, except that a Western blotting experiment using the primary and secondary antibodies as shown in Table 4 was performed to detect the following proteins: p-PI3k, PI3k, p-Akt, Akt, p-Bad, Bad, Bcl-2, and Bcl-$x_L$.

TABLE 4

Primary and secondary antibodies used in Western blotting experiment

| Protein | Primary antibody | Secondary antibody |
| --- | --- | --- |
| p-PI3k | goat anti p-PI3 kinase p85α (Tyr 508) polyclonal antibody (Santa Cruz, Cat. No. sc-12929) | donkey anti-goat IgG-HRP antibody |
| PI3k | rabbit anti PI3 kinase p85α (Z-8) polyclonal antibody (Santa Cruz, Cat. No. sc-423) | goat anti-rabbit IgG-HRP antibody |
| p-Akt | rabbit anti p-Akt (Ser 473) polyclonal antibody (Cell Signaling, USA, Cat. No. 9271) | goat anti-rabbit IgG-HRP antibody |
| Akt | mouse anti Akt monoclonal antibody (BD Biosciences, USA, Cat. No. 610877) | goat anti-mouse IgG-HRP antibody |
| p-Bad | rabbit anti p-Bad (Ser 136) polyclonal antibody (Cell Signaling, USA, Cat. No. 9295) | goat anti-rabbit IgG-HRP antibody |
| Bad | mouse anti Bad monoclonal antibody (BD Biosciences, USA, Cat. No. 610391) | goat anti-mouse IgG-HRP antibody |
| Bcl-2 | mouse anti Bcl-2 monoclonal antibody (BD Biosciences, USA, Cat. No. 610539) | goat anti-mouse IgG-HRP antibody |
| Bcl-$x_L$ | mouse anti Bcl-$x_L$ (H-5) monoclonal antibody (Santa Cruz, Cat. No. sc-8392) | goat anti-mouse IgG-HRP antibody |
| α-tubulin | mouse anti α-tubulin (B-7) monoclonal antibody (Santa Cruz, USA, Cat. No. sc-5286) | goat anti-mouse IgG-HRP antibody |

Figure 12:
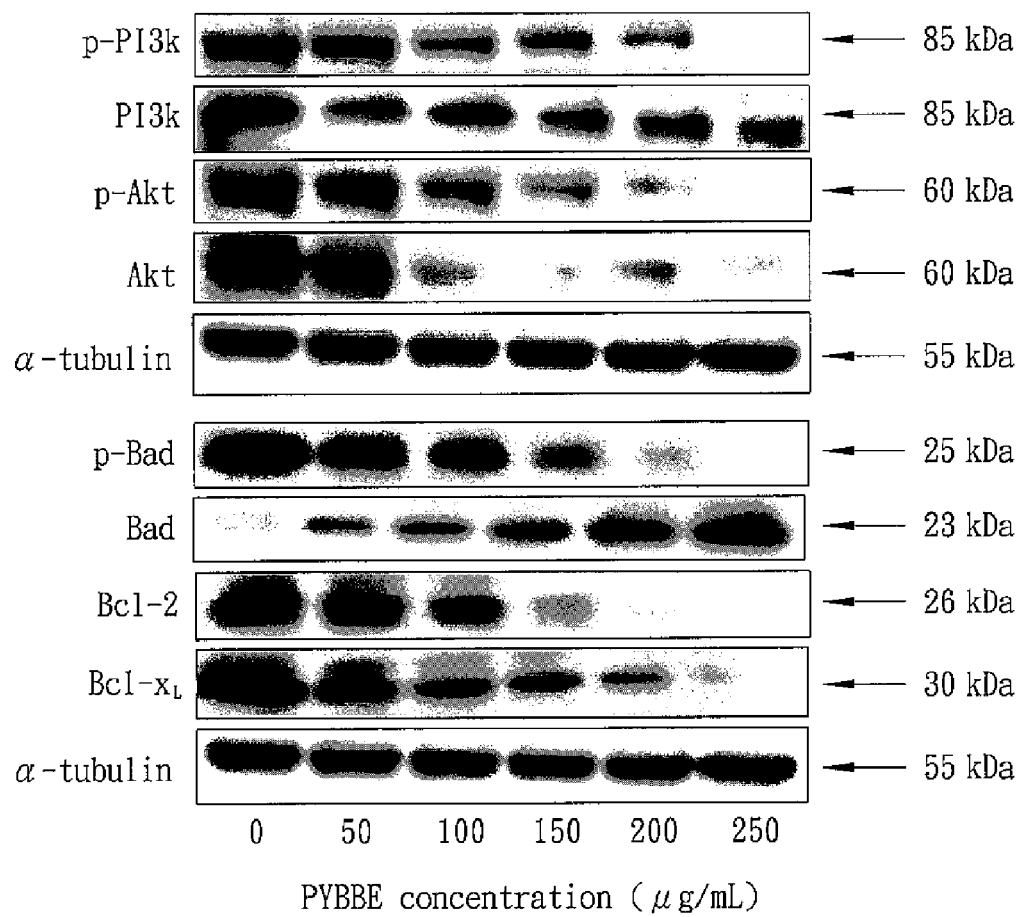
FIG. 12 is a Western blot showing the expression levels of p-PI3k, PI3k, p-Akt, Akt, p-Bad, Bad, Bcl-2, and Bcl-$x_L$ in HA22T cells treated with different concentrations of PYBBE.

Results:

FIG. 12 is a Western blot showing the expression levels of p-PI3k, PI3k, p-Akt, Akt, p-Bad, Bad, Bcl-2, and Bcl-$x_L$ in HA22T cells treated with different concentrations of PYBBE. As shown in FIG. 12, the expression levels of p-PI3k, PI3k, p-Akt, Akt, p-Bad, Bcl-2, and Bcl-$x_L$ in HA22T cells of each of groups 1-5 are lower than those in HA22T cells of the control group. In addition, the expression level of Bad in HA22T cells of each of groups 1-5 is higher than that in HA22T cells of the control group. Therefore, the applicants infer that: PYBBE of this invention is able to sufficiently lower the expression of p-PI3k, PI3k, p-Akt, Akt, p-Bad, Bcl-2, and Bcl-$x_L$, and to sufficiently enhance the expression of Bad, thereby being further capable of inhibiting activation of the cell survival signal transduction pathway so as to reduce survival of HA22T cells.

Example 7

Effect of Product Containing Extract from *Zanthoxylum avicennae* (Lam.) DC. on Metastasis of HA22T Cells In order to understand the effect of PYBBE according to this invention on metastasis of HA22T cells, the following experiments were performed.

A. Cell Migration Assay

HA22T cells were divided into 6 groups including a control group and five experimental groups (i.e., groups 1-5). Each group of HA22T cells was placed in a Petri dish (diameter: 6 cm) containing DMEM (supplemented with 10% FBS, 1.5 g/L $NaHCO_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% $CO_2$). When the cell density reached about 80% confluence, the old medium was replaced with fresh DMEM (supplemented with 1% CCS, 1.5 g/L $NaHCO_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% $CO_2$) for 24 hours, the medium was removed, followed by washing twice with PBS. 1% trypsin-EDTA was added so as to detach the cells from the Petri dish. Subsequently, 1 mL of DMEM (supplemented with 1% CCS, 1.5 g/L $NaHCO_3$, 0.2 mM nonessential amino acids, 2.0 mM glutamine, 100 U/mL penicillin G, and 100 μg/mL streptomycin) was added. Number of the total cells was counted. For each group, dilution was performed using DMEM (supplemented with 1% CCS, 1.5 g/L $NaHCO_3$, 0.2 mM nonessential amino acids, 2.0 mM glutamine, 100 U/mL penicillin G, and 100 μg/mL streptomycin) so that a cell solution having a concentration of $30 \times 10^4$ cell/mL was formed.

Cell migration assay was conducted using a 48-well Boyden chamber (Neuro Probe Inc., MD, USA). First, 32 μL of DMEM (supplemented with 10% CCS, 1.5 g/L $NaHCO_3$, 0.2 mM nonessential amino acids, 2.0 mM glutamine, 100 U/mL penicillin G, and 100 μg/mL streptomycin) was added into each well of a lower chamber. Afterward, a polycarbonate membrane (pore size: 8 μm, Cat. No. PFB8, Neuro Probe Inc., USA) having a rough surface and a smooth surface was placed onto the lower chamber with the rough surface thereof confronting the lower chamber. A gasket and an upper chamber were sequentially placed over the polycarbonate membrane, followed by securing with screws. 50 μL of the cell solution was added into each well of the upper chamber. A plastic wrap was used to cover the upper chamber, followed by cultivation in an incubator (37° C., 5% $CO_2$) for 4-6 hours. Afterward, the polycarbonate membrane was taken out, and the cells on the rough surface of the polycarbonate membrane were subjected to fixation using methanol for 10 minutes. Staining was conducted by virtue of 0.5% Giemsa (Cat. No. GS-500, Sigma, USA) for 1 hour, followed by washing with dd$H_2O$. The smooth surface of the polycarbonate membrane was wiped clean and was attached to a new Petri dish. The Giemsa stained cells on the rough surface of the polycarbonate membrane were observed and counted using an inverted microscope (CKX41, Olympus, Japan). Relative cell migration percentage (%) was calculated by substituting the number of cells into the following formula:

$$J = (K/L) \times 100 \qquad (4)$$

where
- J=relative cell migration percentage
- K=number of Giemsa stained cells in a respective one of the experimental groups and the control group
- L=number of Giemsa stained cells in the control group B. Cell Invasion Assay Cell invasion assay was conducted generally according to the method as described in the preceding section, entitled "A. Cell migration assay", except that: before the cell solution was added into each well of the upper chamber, 10 μL of matrigel (0.2 mg/mL, Cat. No. 354234, BD Biosciences, USA) was added into each well of the upper chamber and was left standing for 5 hours so as to coagulate; and after the plastic wrap was used to cover the upper chamber, cultivation was performed in an incubator for 7-8 hours. Relative cell invasion percentage (%) was calculated by substituting the number of cells into the following formula:

$$M=(N/O)\times 100 \quad (5)$$

where

M=relative cell invasion percentage

N=number of Giemsa stained cells in a respective one of the experimental groups and the control group O=number of Giemsa stained cells in the control group C. Expression Level of Protein Related to Urokinase Plasminogen Activator Signal Transduction Pathway This experiment was performed generally according to the method as described in the section, entitled "B. Expression level of protein related to cell cycle regulation", of the above Example 3, except that a Western blotting experiment using the primary and secondary antibodies as shown in Table 5 was conducted to detect the following proteins: FGF2, p-MEK-1/2, MEK1, p-ERK, ERK1, tPA, uPA, contactin-1, MMP-9, MMP-2, PAI-1, TIMP-1, TIMP-2, TIMP-3, and TIMP-4.

TABLE 5

Primary and secondary antibodies used in Western blotting experiment

| Protein | Primary antibody | Secondary antibody |
|---|---|---|
| FGF2 | rabbit anti FGF2 (147) polyclonal antibody (Santa Cruz, USA, Cat. No. sc-79) | goat anti-rabbit IgG-HRP antibody |
| p-MEK-1/2 | goat anti p-MEK-1/2 (Ser 218/Ser 222) polyclonal antibody (Santa Cruz, USA, Cat. No. sc-7995) | donkey anti-goat IgG-HRP antibody |
| MEK1 | mouse anti MEK1 monoclonal antibody (BD Biosciences, USA, Cat. No. 610121) | goat anti-mouse IgG-HRP antibody |
| p-ERK | mouse anti p-ERK (E-4) monoclonal antibody (Santa Cruz, USA, Cat. No. sc-7383) | goat anti-mouse IgG-HRP antibody |
| ERK1 | mouse anti ERK1 monoclonal antibody (BD Biosciences, USA, Cat. No. 610408) | goat anti-mouse IgG-HRP antibody |
| tPA | goat anti tPA (C-16) polyclonal antibody (Santa Cruz, USA, Cat. No. sc-5239) | donkey anti-goat IgG-HRP antibody |
| uPA | rabbit anti uPA (H-140) polyclonal antibody (Santa Cruz, Cat. No. sc-14019) | goat anti-rabbit IgG-HRP antibody |
| contactin-1 | goat anti contactin-1 (N-19) polyclonal antibody (Santa Cruz, USA, Cat. No. sc-20296) | donkey anti-goat IgG-HRP antibody |
| MMP-9 | rabbit anti MMP-9 polyclonal antibody (Chemicon, Cat. No. AB19016) | goat anti-rabbit IgG-HRP antibody |
| MMP-2 | mouse anti MMP-2 (8B4) monoclonal antibody (Santa Cruz, USA, Cat. No. sc-13595) | goat anti-mouse IgG-HRP antibody |
| PAI-1 | rabbit anti PAI-1 (H-135) polyclonal antibody, Santa Cruz, USA, Cat. No. sc-8979] | goat anti-rabbit IgG-HRP antibody |
| TIMP-1 | rabbit anti TIMP-1 (H-150) polyclonal antibody, Santa Cruz, Cat. No. sc-5538] | goat anti-rabbit IgG-HRP antibody |
| TIMP-2 | rabbit anti TIMP-2 (H-140) polyclonal antibody (Santa Cruz, USA, Cat. No. sc-5539) | goat anti-rabbit IgG-HRP antibody |
| TIMP-3 | goat anti TIMP-3 (C-20) polyclonal antibody (Santa Cruz, USA, Cat. No. sc-6836) | donkey anti-goat IgG-HRP antibody |

TABLE 5-continued

Primary and secondary antibodies used in Western blotting experiment

| Protein | Primary antibody | Secondary antibody |
|---|---|---|
| TIMP-4 | goat anti TIMP-4 (C-16) polyclonal antibody (Santa Cruz, USA, Cat. No. sc-9375) | donkey anti-goat IgG-HRP antibody |
| α-tubulin | mouse anti α-tubulin (B-7) monoclonal antibody (Santa Cruz, USA, Cat. No. sc-5286) | goat anti-mouse IgG-HRP antibody |

D. Expression Level of Protein Related to Mitogen-Activated Protein Kinase (MAPK) Signal Transduction Pathway This experiment was performed generally according to the method as described in the section, entitled "B. Expression level of protein related to cell cycle regulation", of the above Example 3, except that a Western blotting experiment using the primary and secondary antibodies as shown in Table 6 was conducted to detect the following proteins: p-ERK, ERK1, JNK, p-JNK, p-p38, and p38α.

TABLE 6

Primary and secondary antibodies used in Western blotting experiment

| Protein | Primary antibody | Secondary antibody |
|---|---|---|
| p-ERK | mouse anti p-ERK (E-4) monoclonal antibody (Santa Cruz, USA, Cat. No. sc-7383) | goat anti-mouse IgG-HRP antibody |
| ERK1 | mouse anti ERK1 monoclonal antibody (BD Biosciences, USA, Cat. No. 610408) | goat anti-mouse IgG-HRP antibody |
| JNK | rabbit anti JNK (FL) polyclonal antibody (Santa Cruz, USA, Cat. No. sc-571) | goat anti-rabbit IgG-HRP antibody |
| p-JNK | mouse anti p-JNK (G-7) monoclonal antibody (Santa Cruz, USA, Cat. No. sc-6254) | goat anti-mouse IgG-HRP antibody |
| p-p38 | mouse anti p-p38 (D-8) monoclonal antibody (Santa Cruz, USA, Cat. No. sc-7973) | goat anti-mouse IgG-HRP antibody |
| p38α | rabbit anti p38α (C-20) polyclonal antibody (Santa Cruz, USA, Cat. No. sc-535) | goat anti-rabbit IgG-HRP antibody |
| α-tubulin | mouse anti α-tubulin (B-7) monoclonal antibody (Santa Cruz, USA, Cat. No. sc-5286) | goat anti-mouse IgG-HRP antibody |

E. Expression Levels of NF-κB p65 and p-NF-κB p65

This experiment was conducted generally according to the method as described in the section, entitled "B. Expression level of protein related to cell cycle regulation", of the above Example 3, except that a Western blotting experiment using the primary and secondary antibodies as shown in Table 7 was performed to detect the following proteins: NF-κB p65 and p-NF-κB p65.

TABLE 7

Primary and secondary antibodies used in Western blotting experiment

| Protein | Primary antibody | Secondary antibody |
|---|---|---|
| NF-κB p65 | mouse anti NF-κB p65 monoclonal antibody (BD Biosciences, USA, Cat. No. 610868) | goat anti-mouse IgG-HRP antibody |

TABLE 7-continued

Primary and secondary antibodies used in Western blotting experiment

| Protein | Primary antibody | Secondary antibody |
| --- | --- | --- |
| p-NF-κB p65 | rabbit anti p-NF-κB p65 (Ser 536) monoclonal antibody (Cell Signaling, USA, Cat. No. 3033S) | goat anti-rabbit IgG-HRP antibody |
| α-tubulin | mouse anti α-tubulin (B-7) monoclonal antibody (Santa Cruz, USA, Cat. No. sc-5286) | goat anti-mouse IgG-HRP antibody |

Figure 13A:
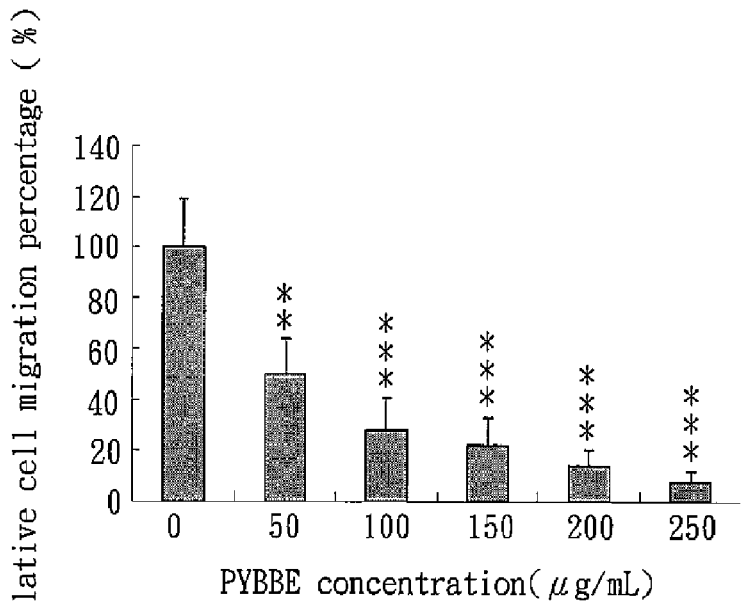
FIGS. 13(A) and 13(B) respectively show the relative cell migration percentage and the relative cell invasion percentage of HA22T cells treated with different concentrations of PYBBE, in which the relative cell migration percentage and the relative cell invasion percentage are expressed as mean±SEM; and the symbols "* *" and "* * *" respectively represent $p<0.01$ and $p<0.001$.
Figure 13B:
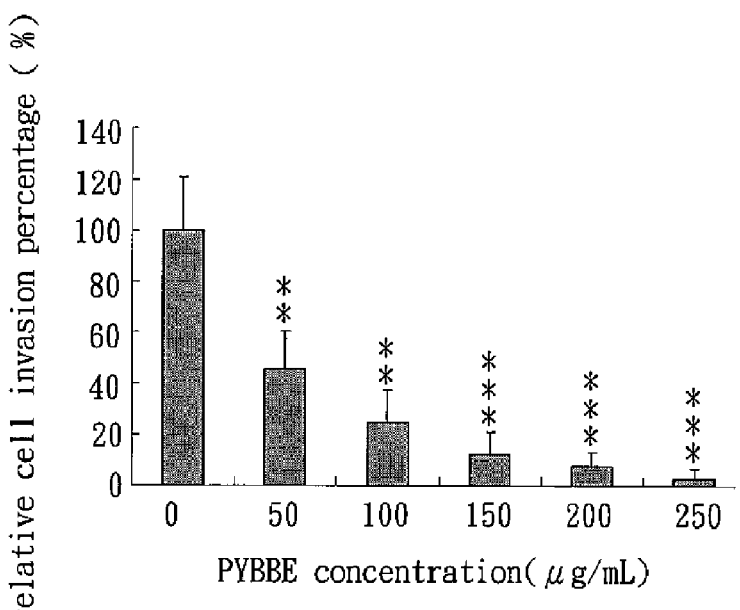

Results:

FIGS. 13(A) and 13(B) respectively show the relative cell migration percentages and the relative cell invasion percentages of HA22T cells treated with different concentrations of PYBBE. As shown in FIGS. 13(A) and 13(B), the relative cell migration percentage and the relative cell invasion percentage of HA22T cells in each of groups 1-5 are significantly lower than those of HA22T cells in the control group. Particularly, the relative cell migration percentage and the relative cell invasion percentage of HA22T cells in group 5 are the lowest (i.e., 7.5% and 3.44%, respectively). The experimental results of sections A and B of Example 7 manifest that there is a positive dose-effect relationship between the dose of PYBBE and the effect of inhibiting the migration and the invasion of HA22T cells.

Figure 14:
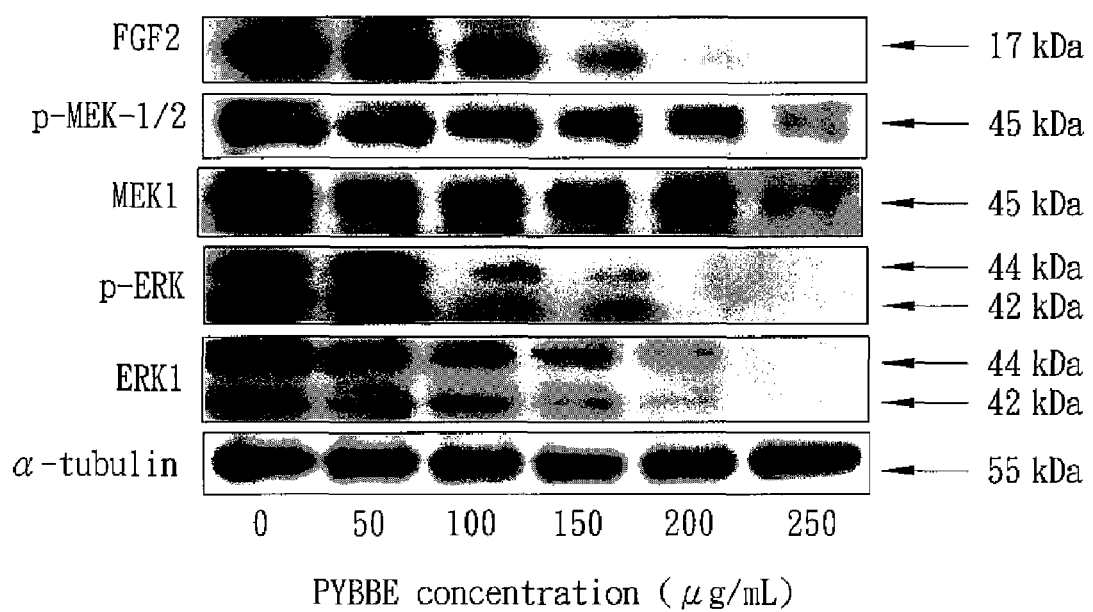
FIG. 14 is a Western blot showing the expression levels of FGF2, p-MEK-1/2, MEK1, p-ERK, and ERK1 in HA22T cells treated with different concentrations of PYBBE.

FIG. 14 is a Western blot showing the expression levels of FGF2, p-MEK-1/2, MEK1, p-ERK, and ERK1 in HA22T cells treated with different concentrations of PYBBE. As shown in FIG. 14, the expression levels of FGF2, p-MEK-1/2, MEK1, p-ERK, and ERK1 in HA22T cells of each of groups 1-5 are lower than those in HA22T cells of the control group, and the expression levels of FGF2, p-MEK-1/2, MEK1, p-ERK, and ERK1 decrese when PYBBE concentration increases. The aforementioned experimental results reveal that there is a positive dose-effect relationship between the dose of PYBBE and the effect of reducing the expression levels of FGF2, p-MEK-1/2, MEK1, p-ERK, and ERK1. The applicants hence preliminarily infer that: PYBBE of this invention is able to sufficiently reduce the expression of FGF2, p-MEK-1/2, MEK1, p-ERK, and ERK1, thereby being effective in inhibiting activation of the urokinase plasminogen activator signal transduction pathway so as to lower the migration and invasion abilities of HA22T cells.

Figure 15:
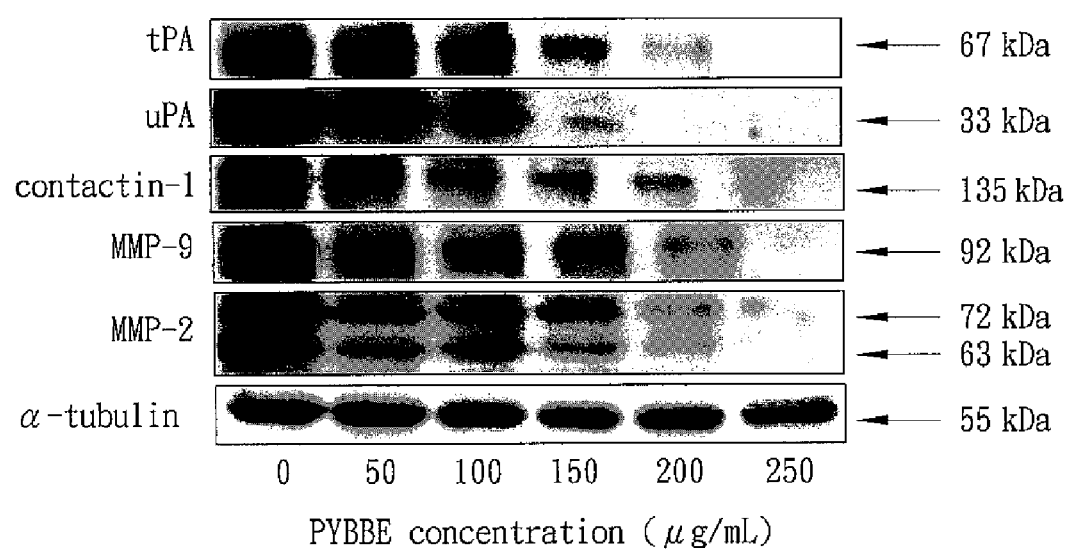
FIG. 15 is a Western blot showing the expression levels of tPA, uPA, contactin-1, MMP-9, and MMP-2 in HA22T cells treated with different concentrations of PYBBE.

FIG. 15 is a Western blot showing the expression levels of tPA, uPA, contactin-1, MMP-9, and MMP-2 in HA22T cells treated with different concentrations of PYBBE. As shown in FIG. 15, the expression levels of tPA, uPA, contactin-1, MMP-9, and MMP-2 in HA22T cells of each of groups 1-5 are lower than those in HA22T cells of the control group, and the expression levels of tPA, uPA, contactin-1, MMP-9, and MMP-2 decrease when PYBBE concentration increases. The aforesaid experimental results indicate that: there is a positive dose-effect relationship between the dose of PYBBE and the effect of lowering the expression levels of tPA, uPA, contactin-1, MMP-9, and MMP-2. Consequently, the applicants preliminarily deduce that: PYBBE of this invention is able to sufficiently lower the expression of tPA, uPA, and contactin-1 (namely, the proteins related to the urokinase plasminogen activator signal transduction pathway), thereby being capable of further sufficiently reducing the expression of MMP-9 and MMP-2 so as to weaken the migration and invasion abilities of HA22T cells.

Figure 16:
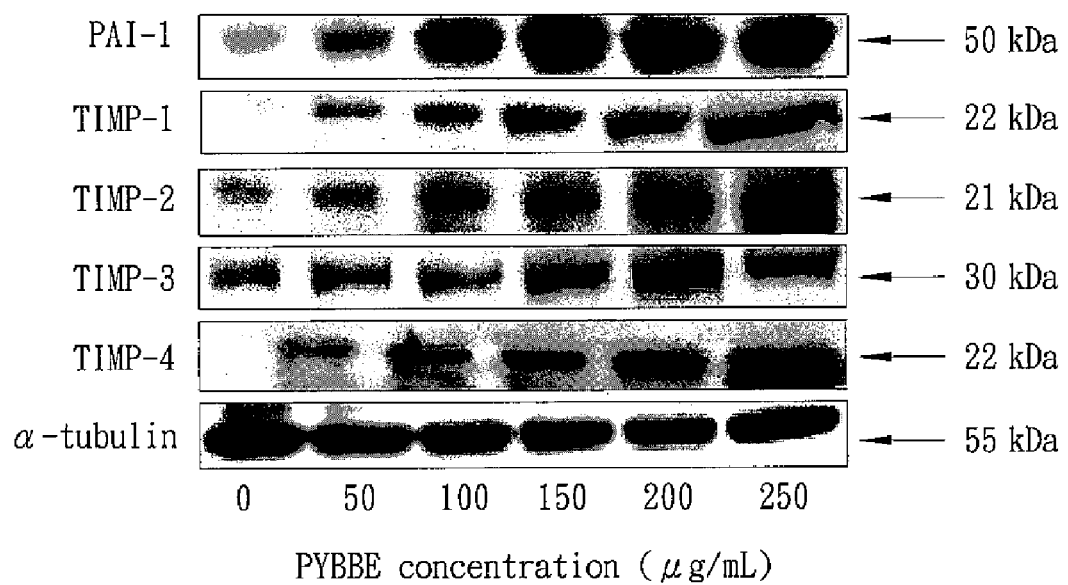
FIG. 16 is a Western blot showing the expression levels of PAI-1, TIMP-1, TIMP-2, TIMP-3, and TIMP-4 in HA22T cells treated with different concenctrations of PYBBE.

FIG. 16 is a Western blot showing the expression levels of PAI-1, TIMP-1, TIMP-2, TIMP-3, and TIMP-4 in HA22T cells treated with different concenctrations of PYBBE. As shown in FIG. 16, the expression levels of PAI-1, TIMP-1, TIMP-2, TIMP-3, and TIMP-4 in HA22T cells of each of groups 1-5 are higher than those in HA22T cells of the control group, and the expression levels of PAI-1, TIMP-1, TIMP-2, TIMP-3, and TIMP-4 increase when PYBBE concentration inceases. The aforementioned experimental results manifest that: there is a positive dose-effect relationship between the dose of PYBBE and the effect of increasing the expression levels of PAI-1, TIMP-1, TIMP-2, TIMP-3, and TIMP-4. The applicants therefore preliminarily presume that: PYBBE of this invention is able to sufficiently enhance the expression of PAI-1, TIMP-1, TIMP-2, TIMP-3, and TIMP-4, thereby being capable of further inhibiting the activity of MMP-9 and MMP-2 so as to reduce the migration and invasion abilities of HA22T cells.

Figure 17:
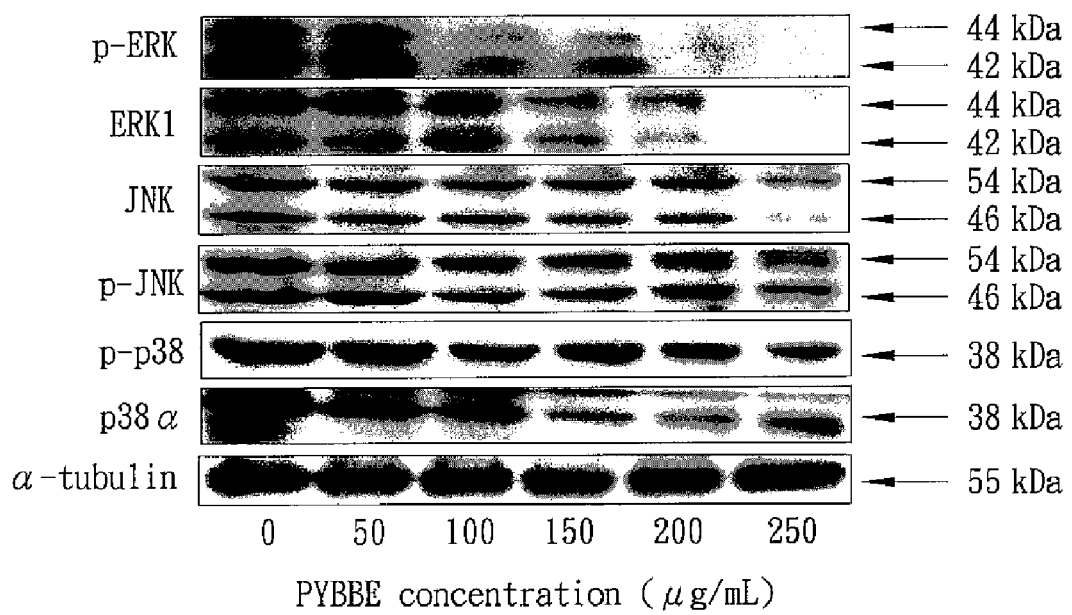
FIG. 17 is a Western blot showing the expression levels of p-ERK, ERK1, JNK, p-JNK, p-p38, and p38α in HA22T cells treated with different concentrations of PYBBE.

FIG. 17 is a Western blot showing the expression levels of p-ERK, ERK1, JNK, p-JNK, p-p38, and p38α in HA22T cells treated with different conecntrations of PYBBE. As shown in FIG. 17, the expression levels of p-ERK, ERK1, JNK, p-JNK, p-p38, and p38α in HA22T cells of each of groups 1-5 are lower than those in HA22T cells of the control group. Thus, the applicants deduce from the experimental results of section D of Example 7 that: PYBBE of this invention is able to sufficiently reduce the expression of p-ERK, ERK1, JNK, p-JNK, p-p38, and p38α, thereby being capable of further inhibiting activation of MAPK signal transduction pathway so as to weaken the migration and invasion abilities of HA22T cells.

Figure 18:
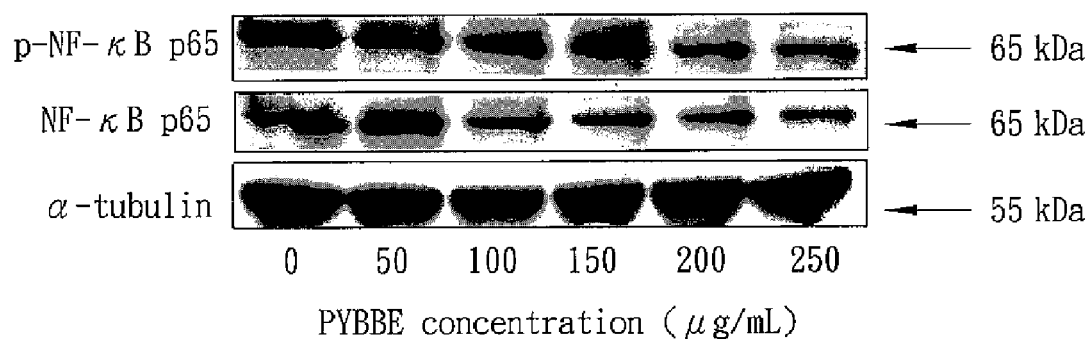
FIG. 18 is a Western blot showing the expression levels of NF-κB p65 and p-NF-κB p65 in HA22T cells treated with different concentrations of PYBBE.

FIG. 18 is a Western blot showing the expression levels of NF-κB p65 and p-NF-κB p65 in HA22T cells treated with different concentrations of PYBBE. As shown in FIG. 18, the expression levels of NF-κB p65 and p-NF-κB p65 in HA22T cells of each of groups 1-5 are lower than those in HA22T cells of the control group, and the expression levels of NF-κB p65 and p-NF-κB p65 decrease when PYBBE concentration increases. The experimental results of section E of Example 7 reveal that: there is a positive dose-effect relationship between the dose of PYBBE and the effect of lowering the expression levels of NF-κB p65 and p-NF-κB p65. The applicants hence preliminarily infer that: PYBBE of this invention is able to sufficiently lower the expression of NF-κB p65 and p-NF-κB p65, thereby being effective in reducing the migration and invasion abilities of HA22T cells.

Example 8

Effect of Product Containing Extract from *Zanthoxylum avicennae* (Lam.) on β-Catenin Signal Transduction Pathway in HA22T Cells In order to further examine whether the effect of PYBBE according this invention on metastasis of HA22T cells is associated with β-catenin signal transduction pathway, the following experiments were conducted.

A. Expression Level of Protein Related to β-Catenin Signal Transduction Pathway

This experiment was performed generally according to the method as described in the section, entitled "B. Expression level of protein related to cell cycle regulation", of the above Example 3, except that a Western blotting experiment using the primary and secondary antibodies as shown in Table 8 was conducted to detect the following proteins: β-catenin, GSK-3β, APC, MMP-2, and MMP-9.

TABLE 8

Primary and secondary antibodies used in Western blotting experiment

| Protein | Primary antibody | Secondary antibody |
| --- | --- | --- |
| β-catenin | mouse anti β-catenin (E-5) monoclonal antibody (Santa Cruz, USA, Cat. No. sc-7963) | goat anti-mouse IgG-HRP antibody |
| GSK-3β | rabbit anti GSK-3β (H-76) polyclonal antibody (Santa Cruz, USA, Cat. No. sc-9166) | goat anti-rabbit IgG-HRP antibody |
| APC | mouse anti APC (F-3) monoclonal antibody (Santa Cruz, USA, Cat. No. sc-9998) | goat anti-mouse IgG-HRP antibody |
| MMP-2 | mouse anti MMP-2 (8B4) monoclonal antibody (Santa Cruz, USA, Cat. No. sc-13595) | goat anti-mouse IgG-HRP antibody |
| MMP-9 | rabbit anti MMP-9 polyclonal antibody (Chemicon, Cat. No. AB19016) | goat anti-rabbit IgG-HRP antibody |
| α-tubulin | mouse anti α-tubulin (B-7) monoclonal antibody (Santa Cruz, USA, Cat. No. sc-5286) | goat anti-mouse IgG-HRP antibody |

B. Immunofluorescence Staining Assay

HA22T cells were divided into 6 groups including a control group and five experimental groups (i.e., groups 1-5). Each group of HA22T cells was placed in a Petri dish (diameter: 6 cm) containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 50% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% CO$_2$) for 24 hours, the medium was removed, followed by washing five times with PBS. 2 mL of 4% paraformaldehyde was added, and the fixation reaction was allowed to proceed for 30 minutes. Paraformaldehyde was removed by washing five times with PBS. 2 mL of 2% BSA was added, and the reaction was allowed to proceed for 1 hour. BSA was removed, followed by washing three times with PBS (10 minutes for each time). The mouse anti β-catenin (E-5) monoclonal antibody (Santa Cruz, USA, Cat. No. sc-7963; diluted 200-fold with PBS) serving as the primary antibody was added, and the reaction was allowed to proceed at 37° C. for 2 hours. Afterward, PBS was utilized to wash three times (10 minutes for each time). The fluorescein-labeled goat anti-mouse IgG-HRP antibody (Santa Cruz, USA, Cat. No. sc-2005; diluted 400-fold with PBS) which serves as the secondary antibody was added, and the reaction was allowed proceed at 37° C. for 1 hour. PBS was used to wash three times (10 minutes for each time). 2 mL of 1 μg/mL DAPI (diluted 10000-fold with PBS) was added, and the reaction was allowed to proceed for 1 minute. DAPI was removed, followed by washing three times with PBS (10 minutes for each time). 2 mL of PBS was added into the Petri dish. The cells in the Petri dish were observed using the excitation light (488 nm) for fluorescein and the excitation light (360 nm) for DAPI under a laser scanning spectral confocal microscope (Leica TCS SP2, Germany).

C. Expression Level of β-Catenin in Nucleus and Cytoplasm

HA22T cells were divided into 6 groups including a control group and five experimental groups (i.e., groups 1-5). Each group of HA22T cells was placed in a Petri dish (diameter: 10 cm) containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 80% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 4 hours. Thereafter, a suitable amount of the PYBBE stock solution obtained in the above Example 1 was added into each of the cultures of groups 1-5 so that the cultures of groups 1-5 respectively had final PYBBE concentrations of 50, 100, 150, 200, and 250 μg/mL.

After HA22T cells in each group were cultivated in an incubator (37° C., 5% CO$_2$) for 24 hours, the medium was removed. PBS was used to wash twice. 200 μL of buffer solution I [containing 10 mM Hepes (pH 7.9), 1.5 mM MgCl$_2$, 10 mM KCl, 0.5 mM DTT, 0.2 mM PMSF, 10 μg/mL leupeptin, and 5 mg/mL protease inhibitor] was added, followed by mixing evenly. The resultant cell mixture was placed in a microcentrifuge tube. Subsequently, the microcentrifuge tube containing the cell mixture was placed on ice for 5 minutes. 20 μL of 1% NP40 (Cat. No. I3021, Sigma, Mo., USA) was added, and the reaction was allowed to proceed for 10 minutes. Centrifugation at 4° C. and 14000 rpm was conducted for 15 minutes. The supernatant was used as a cytoplasmic protein sample. The cytoplasmic protein sample was subjected to determination of protein concentration by virtue of Lowry protein assay. The pellet was utilized to prepare a nucleus protein sample.

100 μL of buffer solution II [containing 20 mM Hepes (pH 7.9), 25% glycerol, 420 mM NaCl, 1.5 mM MgCl$_2$, 0.5 mM DTT, 0.2 mM EDTA, 0.2 mM PMSF, 10 μg/mL leupeptin, and 5 mg/mL protease inhibitor] was mixed evenly with the aforesaid pellet. The resultant mixture was placed on ice for 15 minutes, followed by centrifugation at 4° C. and 14000 rpm for 15 minutes. The supernatant thus formed served as a nucleus protein sample. The nucleus protein sample was then subjected to determination of protein concentration via Lowry protein assay.

The cytoplasmic protein sample and the nucleus protein sample were subjected to a Western blotting experiment according to the method as described in the section, entitled "2. Western blotting", of the General Experimental Procedures so as to detect the following proteins: β-catenin, β-actin (serving as an internal control for the cytoplasmic protein sample), and HDAC1 (serving as an internal control for the nucleus protein sample). The primary and secondary antibodies used for each of the aforementioned proteins are shown in Table 9.

TABLE 9

Primary and secondary antibodies used
in Western blotting experiment

| Protein | Primary antibody | Secondary antibody |
| --- | --- | --- |
| β-catenin | mouse anti β-catenin (E-5) monoclonal antibody (Santa Cruz, USA, Cat. No. sc-7963) | goat anti-mouse IgG-HRP antibody |
| β-actin | mouse anti β-actin (C4) monoclonal antibody (Santa Cruz, USA, Cat. No. sc-47778) | goat anti-mouse IgG-HRP antibody |
| HDAC1 | goat anti HDAC1 (C-19) polyclonal antibody (Santa Cruz, USA, Cat. No. sc-6298) | donkey anti-goat IgG-HRP antibody |

D. Expression Level of Protein Related to β-Catenin Degradation

This experiment was conducted generally according to the method as described in the section, entitled "B. Expression level of protein related to cell cycle regulation", of the above Example 3, except that a Western blotting experiment using the primary and secondary antibodies as shown in Table 10 was performed to detect the following proteins: PP2A, PP2B, and β-TrCP/HOS.

TABLE 10

Primary and secondary antibodies used
in Western blotting experiment

| Protein | Primary antibody | Secondary antibody |
| --- | --- | --- |
| PP2A | mouse anti nonmethylated PP2A C subunit (4B7) monoclonal antibody (Cell Signaling, USA, Cat. No. 4957S) | goat anti-mouse IgG-HRP antibody |
| PP2B | mouse anti calcineurin monoclonal antibody (BD Biosciences, USA, Cat. No. 610260) | goat anti-mouse IgG-HRP antibody |
| β-TrCP/HOS | rabbit anti β-TrCP/HOS (H-300) polyclonal antibody (Santa Cruz, USA, Cat. No. sc-15354) | goat anti-rabbit IgG-HRP antibody |
| α-tubulin | mouse anti α-tubulin (B-7) monoclonal antibody (Santa Cruz, USA, Cat. No. sc-5286) | goat anti-mouse IgG-HRP antibody |

E. Effect of Proteasome Inhibitor on Expression Level of β-Catenin

HA22T cells were divided into 7 groups including a normal control group, a blank control group, and five experimental groups (i.e., groups 1-5). Each group of HA22T cells was placed in a Petri dish (diameter: 10 cm) containing DMEM (supplemented with 10% FBS, 1.5 g/L NaHCO$_2$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 80% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 3 hours. Thereafter, a suitable amount of proteasome inhibitor was added into each of the cultures of groups 1-5 so that the cultures of groups 1-5 respectively had final proteasome inhibitor concentrations of 1, 2, 3, 4, and 5 μg/mL. Subsequently, cultivation was conducted for 1 hour. A suitable amount of the PYBBE stock solution obtained in the above Example 1 was added into each of the cultures of the normal control group and groups 1-5 so that each of the cultures of the normal control group and groups 1-5 had a final PYBBE concentration of 100 μg/mL.

After HA22T cells in each group were cultivated in an incubator (37° C., 5% CO$_2$) for 24 hours, the total protein sample of each group was prepared according to the method as described in the section, entitled "1. Preparation of total protein sample", of the General Experimental Procedures. The total protein samples were subjected to a Western blotting experiment according to the method as described in the section, entitled "2. Western blotting", of the General Experimental Procedures so as to detect the following proteins: β-catenin and α-tubulin (serving as an internal control). The primary and secondary antibodies used for each of the aforesaid two proteins are shown in the above Table 8.

F. Co-Immunoprecipitation Assay

HA22T cells were divided into 3 groups including a control group and two experimental groups (i.e., groups 1 and 2). Each group of HA22T cells was placed in a Petri dish (diameter: 10 cm) containing DMEM (supplemented with 10% FBS, 1.5 g/L NaHCO$_3$, 0.1 mM nonessential amino acids, 2.0 mM glutamine, 100 U/mL penicillin G, 100 μg/mL streptomycin, and 10 g/L phenol red), followed by cultivation in an incubator (37° C., 5% CO$_2$). When the cell density reached about 80% confluence, the old medium was replaced with fresh DMEM (supplemented with 1% CCS, 1.5 g/L NaHCO$_3$, 0.2 mM nonessential amino acids, 2.0 mM glutamine, 100 U/mL penicillin G, and 100 μg/mL streptomycin), followed by cultivation for 3 hours. A suitable amount of proteasome inhibitor was added into each of the cultures of the control group and groups 1 and 2, so that each of the cultures of the control group and groups 1 and 2 had a final proteasome inhibitor concentration of 5 μg/mL. Afterward, the cultivation was conducted for 1 hour. A suitable amount of the PYBBE stock solution obtained in the above Example 1 was added into each of the cultures of groups 1 and 2 so that the cultures of groups 1 and 2 respectively had final PYBBE concentrations of 100 and 250 μg/mL.

After HA22T cells in each group were cultivated in an incubator (37° C., 5% CO$_2$) for 24 hours, the total protein sample of each group was prepared generally according to the method as described in the section, entitled "1. Preparation of total protein sample", of the General Experimental Procedures, except that 200 μL of lysis buffer, which contained 1.5 mM MgCl$_2$, 1% Triton X-100, 50 mM HEPES (pH 7.6), 1 mM EDTA, 150 mM NaCl, 10% glycerol, 1 mM NaVO$_3$, mM NaF, 10 mM β-glycerolphosphate, and 5 mg/mL protease inhibitor, was used.

For each group, 100 μg of the total protein sample thereof was added into each of four microcentrifuge tubes, and a suitable amount of lysis buffer without protease inhibitor was added so that the mixture in each of the four microcentrifuge tubes had a final volume of 500 μL. Subsequently, 7 μL of protein G PLUS-agarose (Santa Cruz, USA, Cat. No. sc-2002) was added, followed by vortexing at 4° C. for 1 hour with a vortex mixer (VORTEX-GENIE®2/G-560, Scientific Industries, NY, USA). Centrifugation at 4° C. and 1300 rpm was performed for 30 seconds. The supernatant was then removed. For each group, 2.5 μL of each antibody listed as follows was added into each of the four microcentrifuge tubes: mouse anti β-catenin (E-5) monoclonal antibody (Santa Cruz, USA, Cat. No. sc-7963), rabbit anti GSK-3β (H-76) polyclonal antibody (Santa Cruz, USA, Cat. No. sc-9166), rabbit anti β-TrCP/HOS(H-300) polyclonal antibody (Santa Cruz, USA, Cat. No. sc-15354), and mouse anti APC (F-3) monoclonal antibody (Santa Cruz, USA, Cat. No. sc-9998). Afterward, vortexing at 4° C. overnight with the vortex mixer was conducted. 20 μL of protein G PLUS-agarose was added, followed by vortexing at 4° C. for 2 hours with the vortex mixer. Centrifugation at 4° C. and 1300 rpm was conducted for 30 seconds. After the supernatant was removed, 1 mL of lysis buffer without protease inhibitor was added to wash the pellet, followed by centrifugation at 4° C. and 1300 rpm for 30 seconds. The supernatant thus formed was removed, followed by washing five times with 1 mL of lysis buffer without protease inhibitor. 5 μL of loading dye was added, and the reaction was allowed to proceed at 100° C. for 5 minutes. A Western blotting experiment was performed according to the method as described in the section, entitled "2. Western blotting", of the General Experimental Procedures so as to detect the following proteins: β-catenin, GSK-3β, β-TrCP/HOS, APC, PP2A, and ubiquitin. The primary and secondary antibodies used for each of the aforementioned proteins are shown in Table 11.

TABLE 11

Primary and secondary antibodies used in Western blotting experiment

| Protein | Primary antibody | Secondary antibody |
| --- | --- | --- |
| β-catenin | mouse anti β-catenin (E-5) monoclonal antibody (Santa Cruz, USA, Cat. No. sc-7963) | goat anti-mouse IgG-HRP antibody |
| GSK-3β | rabbit anti GSK-3β (H-76) polyclonal antibody (Santa Cruz, USA, Cat. No. sc-9166) | goat anti-rabbit IgG-HRP antibody |
| β-TrCP/HOS | rabbit anti β-TrCP/HOS (H-300) polyclonal antibody (Santa Cruz, USA, Cat. No. sc-15354) | goat anti-rabbit IgG-HRP antibody |
| APC | mouse anti APC (F-3) monoclonal antibody (Santa Cruz, USA, Cat. No. sc-9998) | goat anti-mouse IgG-HRP antibody |
| PP2A | mouse anti nonmethylated PP2A C subunit (4B7) monoclonal antibody (Cell Signaling, USA, Cat. No. 4957S) | goat anti-mouse IgG-HRP antibody |
| ubiquitin | mouse anti ubiquitin (P4D1) monoclonal antibody (BD Biosciences, USA, Cat. No. 8017) | goat anti-mouse IgG-HRP antibody |

G. Expression Level of β-Catenin Target Gene

This experiment was conducted generally according to the method as described in the section, entitled "B. Expression level of protein related to cell cycle regulation", of the above Example 3, except that a Western blotting experiment using the primary and secondary antibodies as shown in Table 12 was performed to detect the following proteins: TBX3, IL-8, cyclin D1, and c-Myc.

TABLE 12

Primary and secondary antibodies used in Western blotting experiment

| Protein | Primary antibody | Secondary antibody |
| --- | --- | --- |
| TBX3 | rabbit anti TBX3 (H-92) polyclonal antibody (Santa Cruz, USA, Cat. No. sc-48781) | goat anti-rabbit IgG-HRP antibody |
| IL-8 | rabbit anti IL-8 (H-60) polyclonal antibody (Santa Cruz, USA, Cat. No. sc-7922) | goat anti-rabbit IgG-HRP antibody |
| cyclin D1 | mouse anti cyclin D1 (HD11) monoclonal antibody (Santa Cruz, USA, Cat. No. sc-246) | goat anti-mouse IgG-HRP antibody |
| c-Myc | mouse anti c-Myc (C-33) monoclonal antibody (Santa Cruz, USA, Cat. No. sc-42) | goat anti-mouse IgG-HRP antibody |
| α-tubulin | mouse anti α-tubulin (B-7) monoclonal antibody (Santa Cruz, USA, Cat. No. sc-5286) | goat anti-mouse IgG-HRP antibody |

Figure 19:
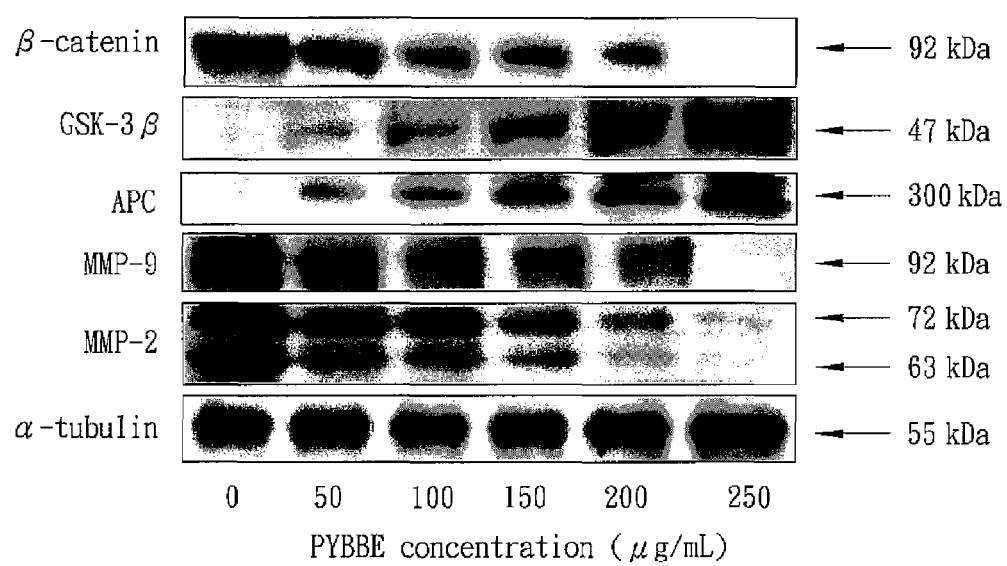
FIG. 19 is a Western blot showing the expression levels of β-catenin, GSK-3β, APC, MMP-2, and MMP-9 in HA22T cells treated with different concentrations of PYBBE.

Results:

FIG. 19 is a Western blot showing the expression levels of β-catenin, GSK-3β, APC, MMP-2, and MMP-9 in HA22T cells treated with different concentrations of PYBBE. As shown in FIG. 19, the expression levels of GSK-3β and APC in HA22T cells of each of groups 1-5 are higher than those in HA22T cells of the control group, and the expression levels of GSK-3β and APC increase when PYBBE concentration increases. Furthermore, the expression levels of β-catenin, MMP-2, and MMP-9 in HA22T cells of each of groups 1-5 are lower than those in HA22T cells of the control group, and the expression levels of β-catenin, MMP-2, and MMP-9 decrease when PYBBE concentration increases. The experimental results of section A of Example 8 reveal that: there are positive dose-effect relationships between the dose of PYBBE and the effect of enhancing the expression levels of GSK-3β and APC, and between the dose of PYBBE and the effect of reducing the expression levels of β-catenin, MMP-2, and MMP-9. The applicants therefore preliminarily deduce that: PYBBE of this invention is able to sufficiently enhance the expression of GSK-3β and APC and to sufficiently reduce the expression of β-catenin, MMP-2, and MMP-9, thereby being further capable of inhibiting the activation of the β-catenin signal transduction pathway so as to weaken the metastasis ability of HA22T cells.

Figure 20:
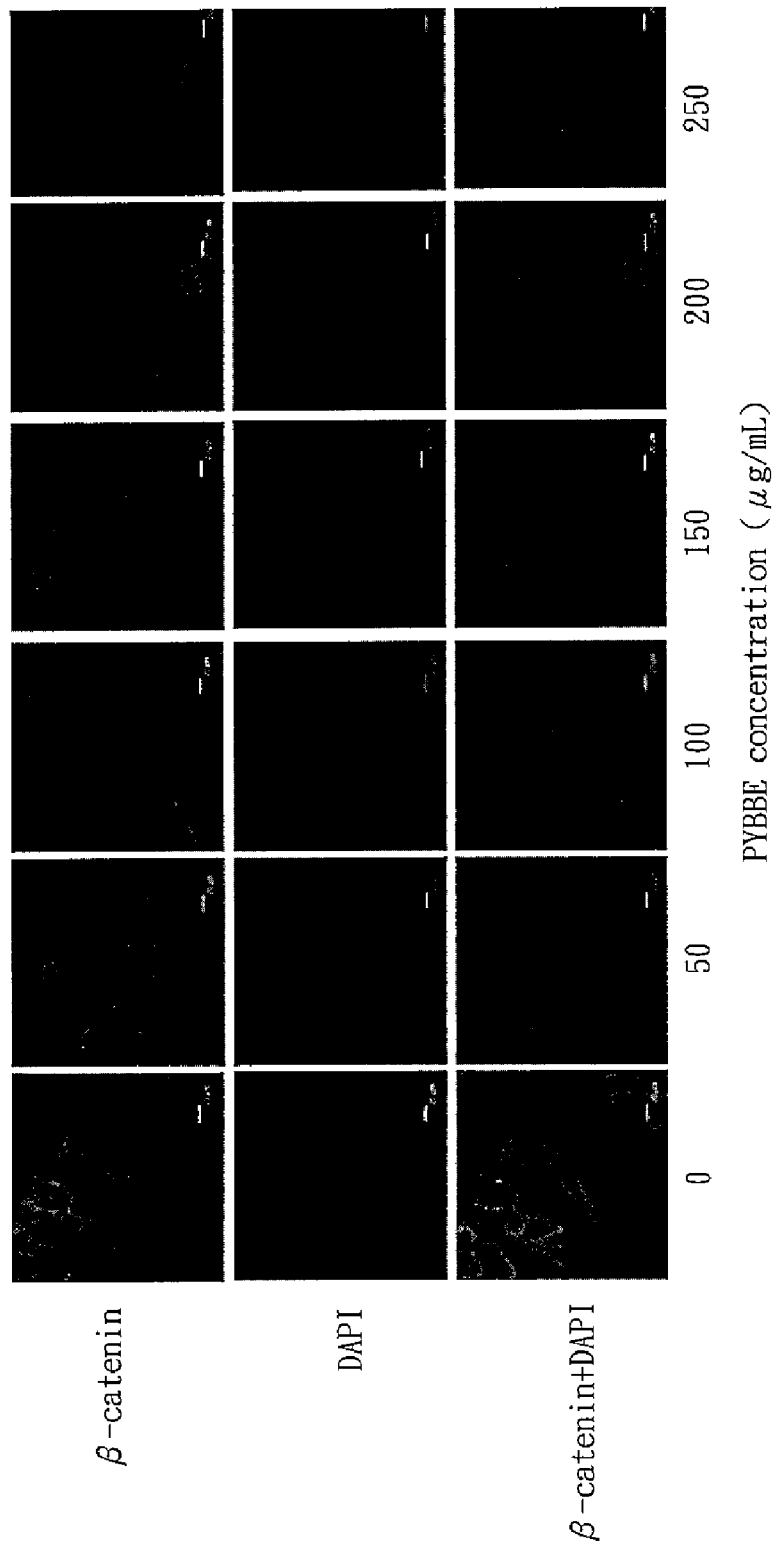
FIG. 20 shows photomicrographs regarding the immunofluorescence staining results of HA22T cells treated with different concentrations of PYBBE, which illustrate the expression level of β-catenin, in which the nucleus stained with DAPI is blue; and β-catenin stained with fluorescein is green.

FIG. 20 shows photomicrographs regarding the immunofluorescence staining results of HA22T cells treated with different concentrations of PYBBE, which illustrate the expression level of β-catenin. As shown in FIG. 20, the expression level of β-catenin in the nucleus of HA22T cells of each of groups 1-5 is lower than that in the nucleus of HA22T cells of the control group, and the expression level of β-catenin decreases when PYBBE concentration increases. Thus, the applicants infer from the experimental results of section B of Example 8 that: PYBBE of this invention is able to sufficiently lower the expression of β-catenin in the nucleus, thereby being further capable of inhibiting the activation of the β-catenin signal transduction pathway so as to reduce the metastasis ability of HA22T cells.

Figure 21A:
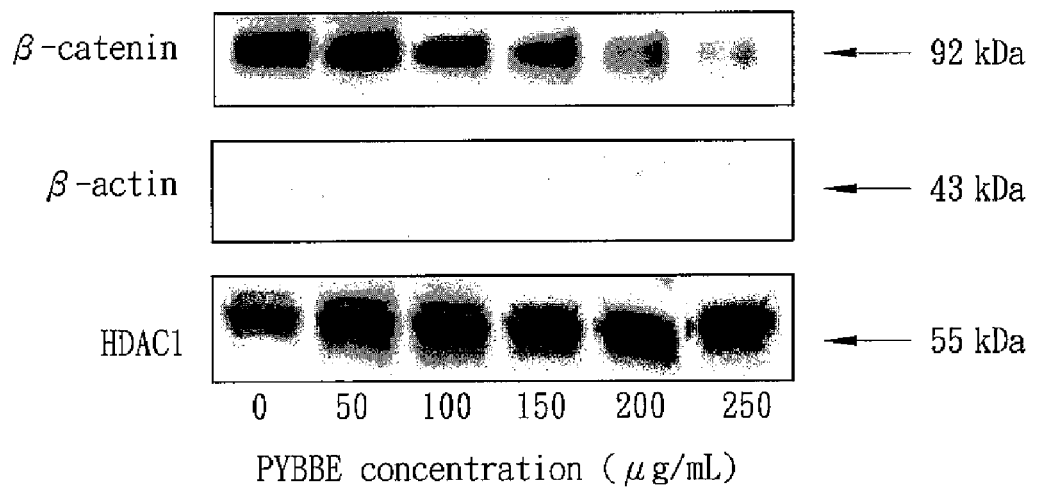
FIGS. 21(A) and 21(B) are Western blots respectively showing the expression level of β-catenin in the nucleus and the cytoplasm of HA22T cells treated with different concentrations of PYBBE.
Figure 21B:
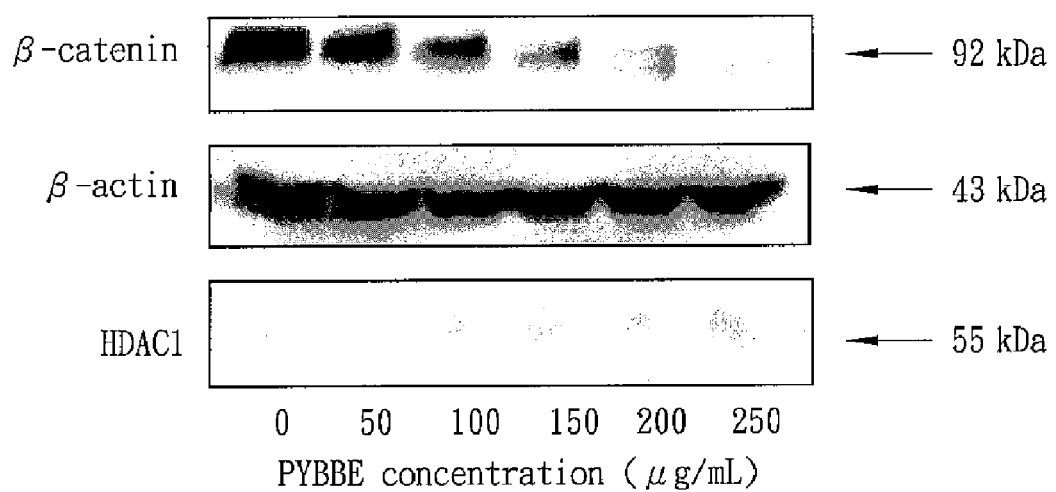

FIGS. 21(A) and 21(B) are Western blots respectively showing the expression level of β-catenin in the nucleus and the cytoplasm of HA22T cells treated with different concentrations of PYBBE. As shown in FIGS. 21(A) and 21(B), the expression level of β-catenin in the nucleus and the cytoplasm of HA22T cells of each of groups 1-5 is lower than that in the nucleus and the cytoplasm of HA22T cells of the control group, and the expression level of β-catenin in the nucleus and the cytoplasm decreases when PYBBE concentration increases. Accordingly, the experimental results of section C of Example 8 indicate that there is a positive dose-effect relationship between the dose of PYBEE and the effect of reducing the expression level of β-catenin in the nucleus and the cytoplasm. The applicants hence preliminarily presume that: PYBBE of this invention is able to sufficiently reduce the expression of β-catenin in the nucleus and the cytoplasm, thereby being further capable of inhibiting the activation of the β-catenin signal transduction pathway so as to weaken the metastasis ability of HA22T cells.

Figure 22:
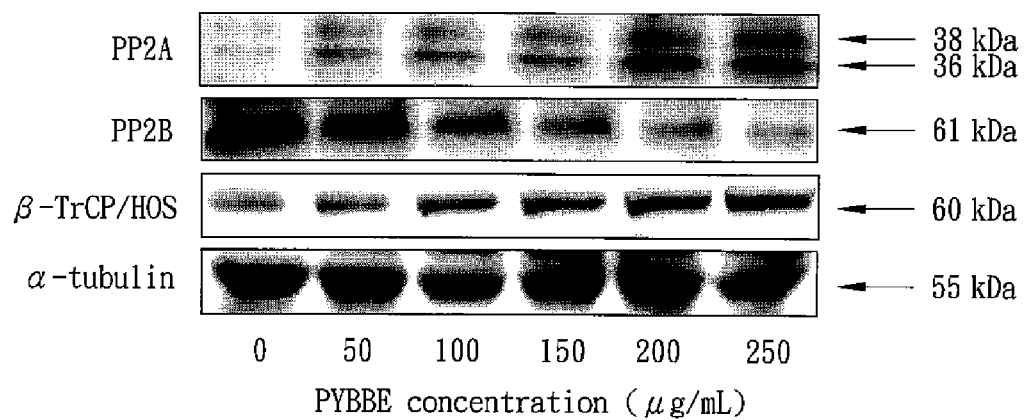
FIG. 22 is a Western blot showing the expression levels of PP2A, PP2B, and β-TrCP/HOS in HA22T cells treated with different concentrations of PYBBE.

FIG. 22 is a Western blot showing the expression levels of PP2A, PP2B, and β-TrCP/HOS in HA22T cells treated with different concentrations of PYBBE. As shown in FIG. 22, the expression levels of PP2A and β-TrCP/HOS in HA22T cells of each of groups 1-5 are higher than those in HA22T cells of the control group, and the expression levels of PP2A and β-TrCP/HOS increase when PYBBE concentration increases. Additionally, the expression level of PP2B in HA22T cells of each of groups 1-5 is lower than that in HA22T cells of the control group, and the expression level of PP2B decreases when PYBBE concentration increases. Accordingly, the experimental results of section D of Example 8 manifest that: there are positive dose-effect relationships between the dose of PYBBE and the effect of increasing the expression levels of PP2A and β-TrCP/HOS, and between the dose of PYBBE and the effect of decreasing the expression level of PP2B. Consequently, the applicants preliminarily deduce that: PYBBE of this invention is able to sufficiently enhance the expression of PP2A and β-TrCP/HOS and to sufficiently reduce the expression of PP2B, thereby being further capable of facilitating the phosphorylation and the degradation of β-catenin so that the activation of the β-catenin signal transduction pathway can be inhibited to reduce the metastasis ability of HA22T cells.

Figure 23:
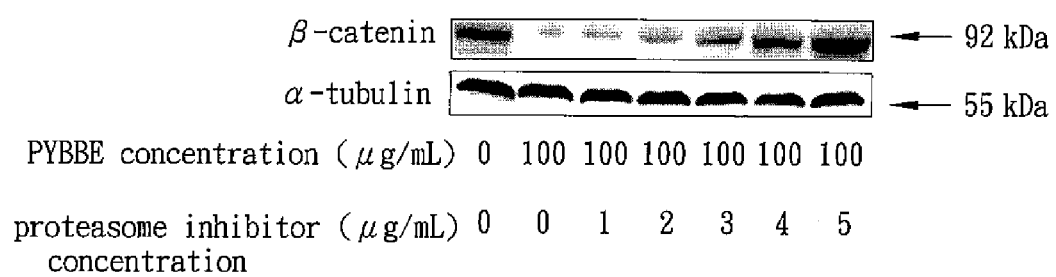
FIG. 23 is a Western blot showing the expression level of β-catenin in HA22T cells treated with different concentrations of proteasome inhibitor and the same concentration of PYBBE.

FIG. 23 is a Western blot showing the expression level of β-catenin in HA22T cells treated with different concentrations of proteasome inhibitor and the same concentration of PYBBE. As shown in FIG. 23, the expression level of β-catenin in HA22T cells of the normal control group is significantly lower than that in HA22T cells of the blank control group. Therefore, PYBBE is able to sufficiently reduce the expression of β-catenin. In addition, the expression level of β-catenin in HA22T cells of each of groups 1-5 is higher than that in HA22T cells of the normal control group, and the expression level of β-catenin increases when the proteasome inhibitor concentration increases. Accordingly, the applicants preliminarily infer from the experimental results of section E of Example 8 that: PYBBE of this invention is able to reduce the amount of β-catenin by faciliating the degradation of β-catenin by proteasome, thereby being capable of inhibiting the activation of the β-catenin signal transduction pathway so as to reduce the metastasis ability of HA22T cells.

Figure 24:
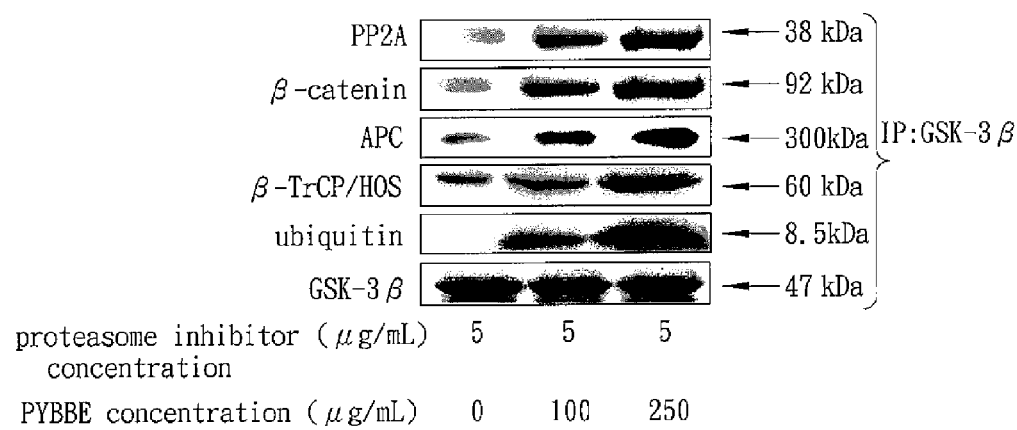
FIG. 24 shows the co-immunoprecipitation result regarding the degree of association of GSK-3β with a respective one of PP2A, β-catenin, APC, β-TrCP/HOS, and ubiquitin in HA22T cells treated with the same concentration of proteasome inhibitor and different concentrations of PYBBE.

FIG. 24 shows the co-immunoprecipitation result regarding the degree of association of GSK-3β with a respective one of PP2A, β-catenin, APC, β-TrCP/HOS, and ubiquitin in HA22T cells treated with the same concentration of proteasome inhibitor and different concentrations of PYBBE. As shown in FIG. 24, the degree of association of GSK-3β with a respective one of PP2A, β-catenin, APC, β-TrCP/HOS, and ubiquitin in HA22T cells of each of groups 1 and 2 is higher than that in HA22T cells of the control group, and the degree of association of GSK-3β with a respective one of PP2A, β-catenin, APC, β-TrCP/HOS, and ubiquitin increases when PYBBE concentration increases.

Figure 25:
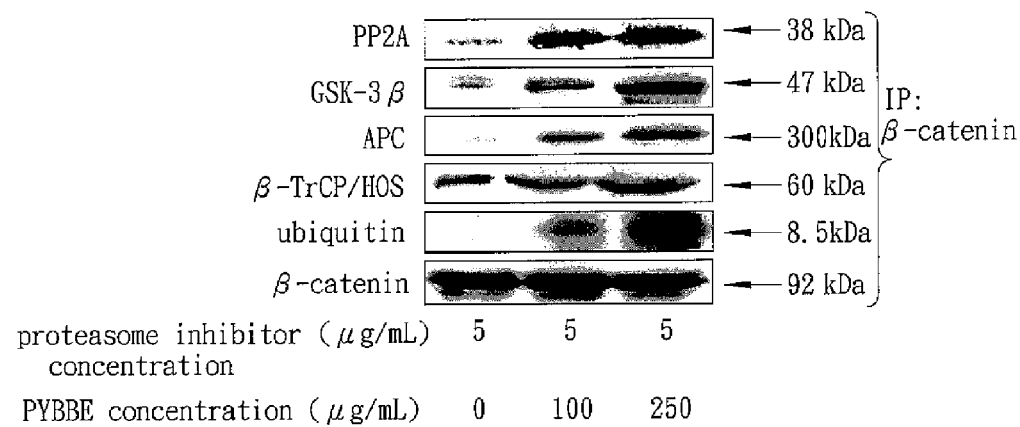
FIG. 25 shows the co-immunoprecipitation result regarding the degree of association of β-catenin with a respective one of PP2A, GSK-3β, APC, β-TrCP/HOS, and ubiquitin in HA22T cells treated with the same concentration of proteasome inhibitor and different concentrations of PYBBE.

FIG. 25 shows the co-immunoprecipitation result regarding the degree of association of β-catenin with a respective one of PP2A, GSK-3β, APC, β-TrCP/HOS, and ubiquitin in HA22T cells treated with the same concentration of proteasome inhibitor and different concentrations of PYBBE. As shown in FIG. 25, the degree of association of β-catenin with a respective one of PP2A, GSK-3β, APC, β-TrCP/HOS, and ubiquitin in HA22T cells of each of groups 1 and 2 is higher than that in HA22T cells of the control group, and the degree of association of β-catenin with a respective one of PP2A, GSK-3β, APC, β-TrCP/HOS, and ubiquitin increases when PYBBE concentration increases.

Figure 26:
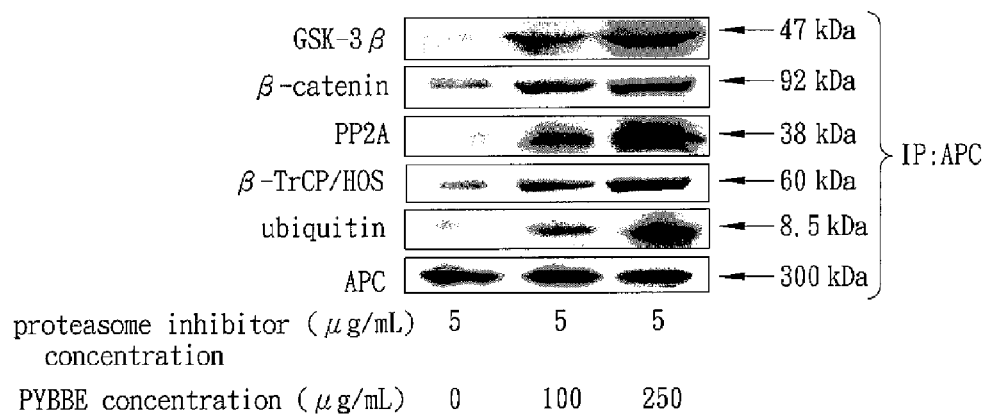
FIG. 26 shows the co-immunoprecipitation result regarding the degree of association of APC with a respective one of GSK-3β, β-catenin, PP2A, β-TrCP/HOS, and ubiquitin in HA22T cells treated with the same concentration of proteasome inhibitor and different concentrations of PYBBE.

FIG. 26 shows the co-immunoprecipitation result regarding the degree of association of APC with a respective one of GSK-3β, β-catenin, PP2A, β-TrCP/HOS, and ubiquitin in HA22T cells treated with the same concentration of proteasome inhibitor and different concentrations of PYBBE. As shown in FIG. 26, the degree of association of APC with a respective one of GSK-3β, β-catenin, PP2A, β-TrCP/HOS, and ubiquitin in HA22T cells of each of groups 1 and 2 is higher than that in HA22T cells of the control group, and the degree of association of APC with a respective one of GSK-3β, β-catenin, PP2A, β-TrCP/HOS, and ubiquitin increases when PYBBE concentration increases.

Figure 27:
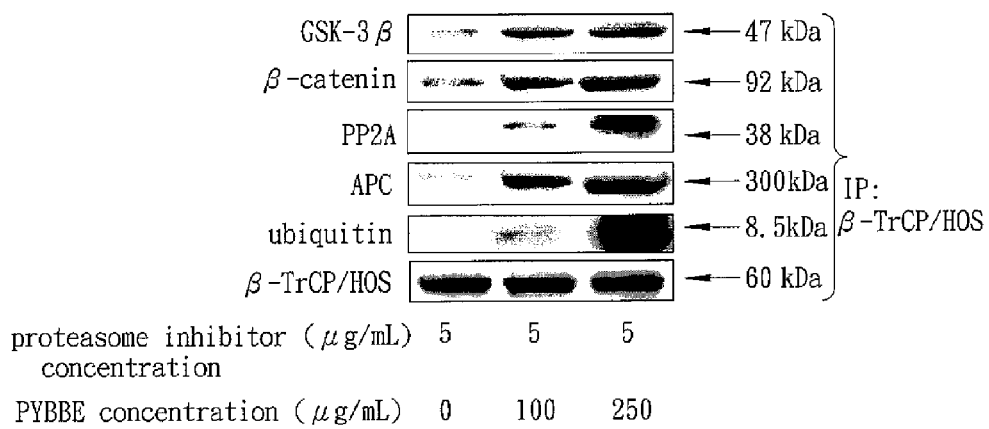
FIG. 27 shows the co-immunoprecipitation result regarding the degree of association of β-TrCP/HOS with a respective one of GSK-3β, β-catenin, PP2A, APC, and ubiquitin in HA22T cells treated with the same concentration of proteasome inhibitor and different concentrations of PYBBE.

FIG. 27 shows the co-immunoprecipitation result regarding the degree of association of β-TrCP/HOS with a respective one of GSK-3β, β-catenin, PP2A, APC, and ubiquitin in HA22T cells treated with the same concentration of proteasome inhibitor and different concentrations of PYBBE. As shown in FIG. 27, the degree of association of β-TrCP/HOS with a respective one of GSK-3β, β-catenin, PP2A, APC, and ubiquitin in HA22T cells of each of groups 1 and 2 is higher than that in HA22T cells of the control group, and the degree of association of β-TrCP/HOS with a respective one of GSK-3β, β-catenin, PP2A, APC, and ubiquitin increases when PYBBE concentration increases.

The applicants hence deduce from the experimental results of section F of Example 8 that: PYBBE of this invention is able to enhance the association between β-catenin and β-catenin phosphorilation-related factors, i.e., β-TrCP/HOS, GSK-3β, APC, and PP2A, and the association of the β-catenin phosphorilation-related factors, and to facilitate the association between β-catenin and ubiquitin, thereby resulting in phosphorilation of β-catenin and being further capable of inducing the degradation of β-catenin by proteasome so that the activation of the β-catenin signal transduction pathway can be inhibited to weaken the metastasis ability of HA22T cells.

Figure 28:
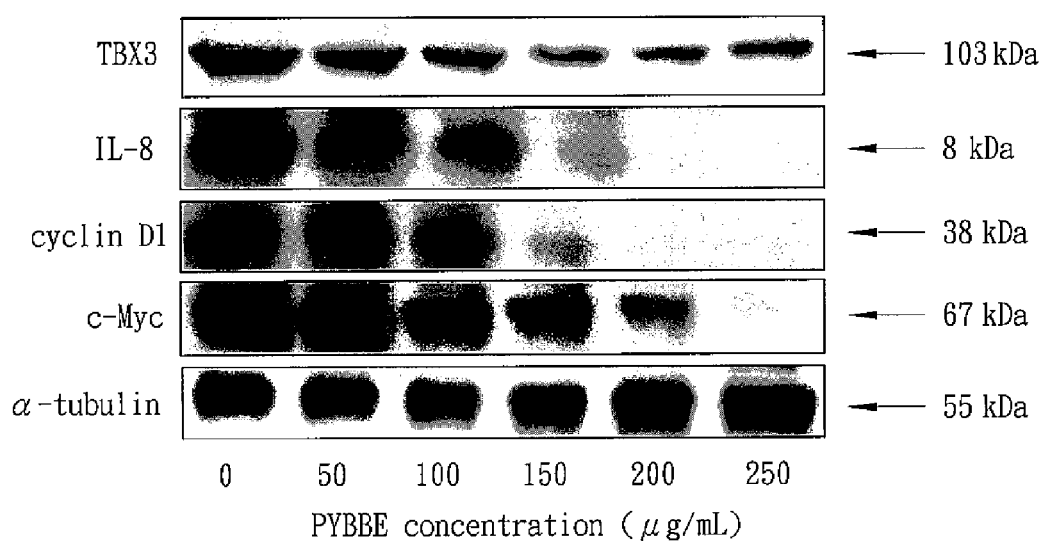
FIG. 28 is a Western blot showing the expression levels of TBX3, IL-8, cyclin D1, and c-Myc (i.e., the expression products of β-catenin target genes) in HA22T cells treated with different concentrations of PYBBE.

FIG. 28 is a Western blot showing the expression levels of TBX3, IL-8, cyclin D1, and c-Myc (i.e., the expression products of β-catenin target genes) in HA22T cells treated with different concentrations of PYBBE. As shown in FIG. 28, the expression levels of TBX3, IL-8, cyclin D1, and c-Myc in HA22T cells of each of groups 1-5 are lower than those in HA22T cells of the control group, and the expression levels of TBX3, IL-8, cyclin D1, and c-Myc decrease when PYBBE concentration increases. Thus, the experimental results of section G of Example 8 reveal that there is a positive dose-effect relationship between the dose of PYBBE and the effect of lowering the expression levels of TBX3, IL-8, cyclin D1, and c-Myc. Consequently, the applicants deduce that: PYBBE of this invention is able to reduce the expression of β-catenin, thereby being further capable of sufficiently lowering the expression of β-catenin target genes (i.e., TBX3, IL-8, cyclin D1, and c-Myc genes) so as to inhibit proliferation and metastasis of HA22T cells Example 9

In Vivo Test for Product Containing Extract from *Zanthoxylum avicennae* (Lam.) DC.

In order to investigate whether the product containing the extract from *Zanthoxylum avicennae* (Lam.) DC. has in vivo anticancer activities, the following experiments were conducted.

A. Effect of PYBBE on Tumor Growth 18 male NU/NU nude mice (a body weight of 20-22 g, at the age of 5 weeks, BioLASCO Taiwan Co., Ltd, Taipei, Taiwan) were raised under the following laboratory conditions: a temperature of 21±2° C., a relative humidity of 30-70%, and a 12 hour light/12 hour dark cycle. The mice were divided into 3 groups including a control group and two experimental groups (i.e., groups 1 and 2). For each group, HA22T cells ($1 \times 10^6$ cells in 100 μl DMEM) were subcutaneously injected into the left flank of each of the mice. On the fourth day after the subcutaneous injection (designated as Day 0), namely, when a tumor reached a volume of about 600 mm$^3$, a suitable amount of PYBBE stock solution obtained in the above Example 1 was orally administered to the mice in groups 1 and 2 respectively at a daily dose of 20 mg/kg and 40 mg/kg. A size (i.e., length and width) of a tumor was measured every three days with calipers during a period of 15 days. The tumor volume was calculated by substituting the length and the width into the following formula:

$$TV = (L \times W^2)/2 \quad (6)$$

where
  L=length
  W=width
  TV=tumor volume

The mice were sacrificed on Day 15 (i.e., 19 days after the subcutaneous injection). Subsequently, the tumors were excised, and were subjected to length, width, and weight measurement. The experimental data were analyzed according to the method as described in the section, entitled "3. Statistical analysis", of the General Experimental Procedures.

B. Effect of PYBBE on Proliferation and Apoptosis of Tumor Cells 0.1 g of the tumor tissue collected from the excised tumor obtained in the preceding section, entitled "A. Effect of PYBBE on tumor growth", was mixed with 1 mL of lysis buffer [containing homogenization buffer A (formulated with 20 mM Tris, 2 mM EDTA, and ddH$_2$O), glycerol, 2-mercaptoethanol, protease inhibitor cocktail tablets (Roche, Cat. No. 04693159001), phosphatase inhibitor cocktail 2 (Sigma, Cat. No. P-5726, 100× stock)], followed by grinding for several seconds with a grinding machine (Polytron® PT-MR 2100, Switzerland). Centrifugation at 4° C. and 12000 rpm was performed for 40 minutes. The supernatant was collected and served as the total protein sample. The total protein sample of each group was subjected to a Western blotting experiment according to the method as described in the section, entitled "2. Western blotting", of the General Experimental Procedures so as to detect the following proteins: PCNA, c-Fos, c-Myc, p27, p53, caspase-8, caspase 9, and caspase 3. The primary and secondary antibodies used for the aforementioned proteins are shown in the above tables.

Figure 29A:
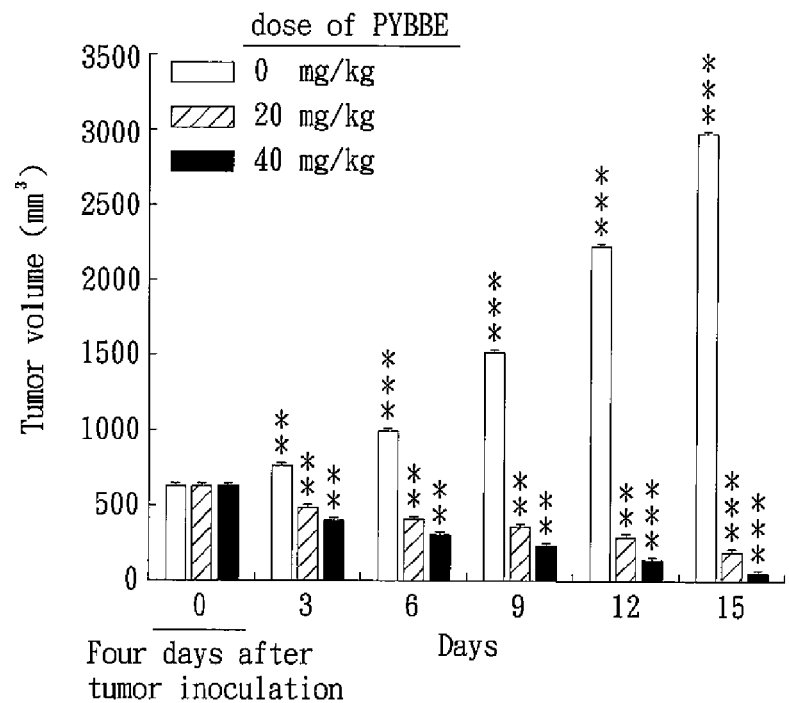
FIGS. 29(A) and 29(B) are bar diagrams respectively showing the tumor volume and the tumor weight regarding the mice treated with different doses of PYBBE, in which the symbols "* *" and "* * *" respectively represent $p<0.01$ and $p<0.001$.
Figure 29B:
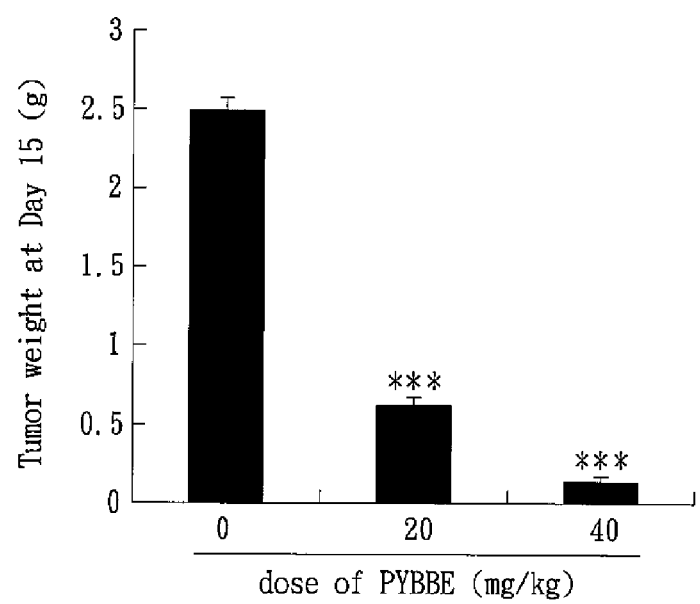

Results:

FIGS. 29(A) and 29(B) are bar diagrams respectively showing the tumor volume and the tumor weight regarding the mice treated with different doses of PYBBE. As shown in FIGS. 29 (A) and 29(B), the tumor volume and the tumor weight regarding the mice in each of groups 1 and 2 are lower than those regarding the mice in the control group, and the tumor volume and the tumor weight decrease when the dose of PYBBE increases. Therefore, the experimental results of section A of Example 9 indicate that there is a positive dose-effect relationship between the dose of PYBBE and the effect of inhibiting the tumor growth.

Figure 30:
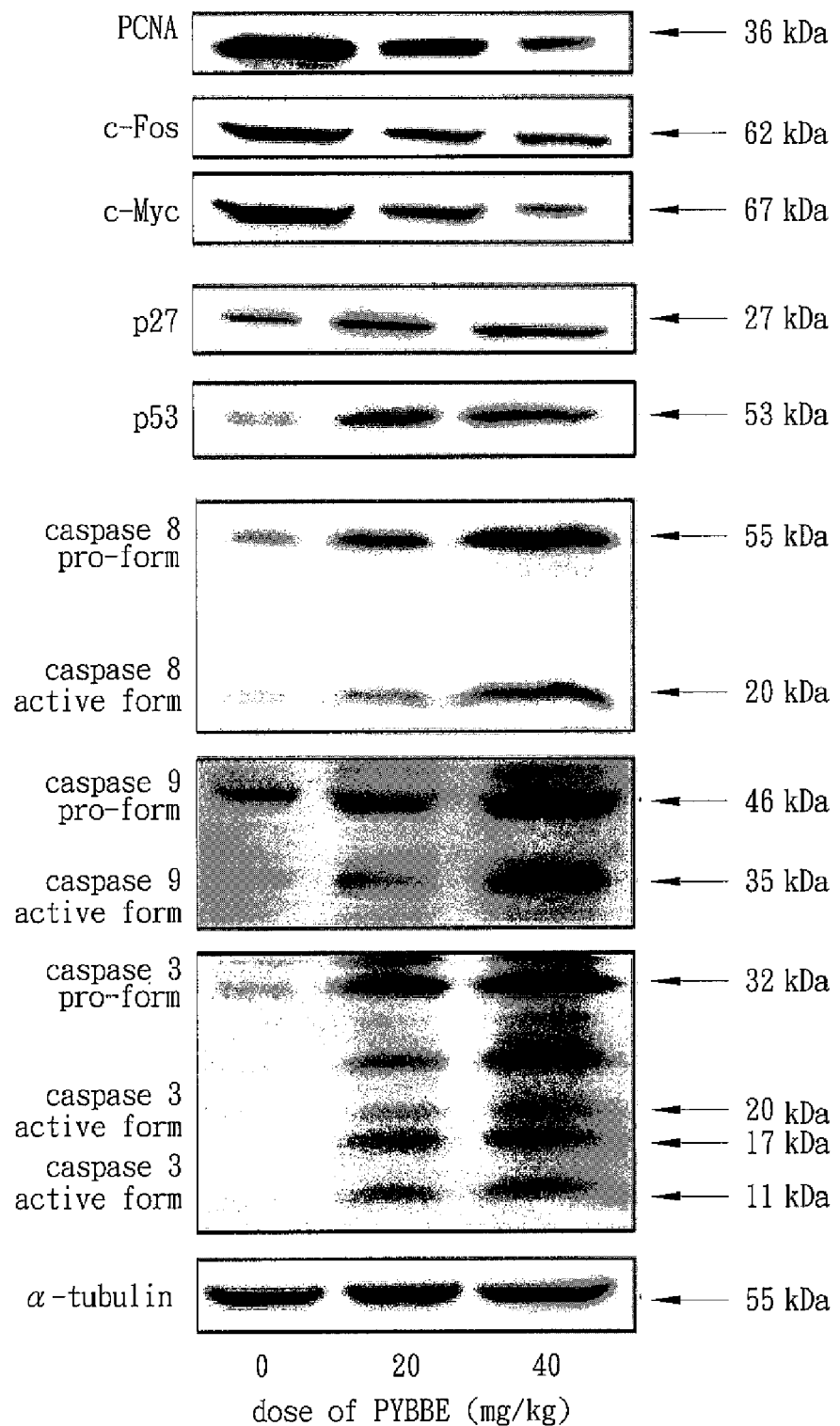
FIG. 30 is a Western blot showing the expression levels of PCNA, c-Fos, c-Myc, p27, p53, caspase-8 (the pro-form and the active form), caspase 9 (the pro-form and the active form), and caspase 3 (the pro-form and the two active forms) in tumor cells of the mice treated with different doses of PYBBE.

FIG. 30 is a Western blot showing the expression levels of PCNA, c-Fos, c-Myc, p27, p53, caspase-8 (the pro-form and the active form), caspase 9 (the pro-form and the active form), and caspase 3 (the pro-form and the two active forms) in the tumor cells of the mice treated with different doses of PYBBE. As shown in FIG. 30, the expression levels of p27, p53, caspase-8 (the pro-form and the active form), caspase 9 (the pro-form and the active form), and caspase 3 (the pro-form and the two active forms) in the tumor cells of the mice of each of groups 1 and 2 are higher than those in the tumor cells of the mice of the control group, and the expression levels of p27, p53, caspase-8 (the pro-form and the active form), caspase 9 (the pro-form and the active form), and caspase 3 (the pro-form and the two active forms) increase when the dose of PYBBE increases. In addition, the expression levels of PCNA, c-Fos, and c-Myc in the tumor cells of the mice of each of groups 1 and 2 are lower than those in the tumor cells of the mice of the control group, and the expression levels of PCNA, c-Fos, and c-Myc decrease when the dose of PYBBE increases. The in vivo experimental results of section B of Example 9 are consistent with the in vitro results of the preceding examples. Thus, PYBBE of this invention is able to suppress tumor cell proliferation in vivo and to increase tumor cell apoptosis in vivo. By virtue of the in vivo tests, the applicants preliminarily deduce that PYBBE of this invention is effective in cancer treatment.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

What is claimed is:

1. A product containing an extract from *Zanthoxylum avicennae* (Lam.) DC., which is prepared by a process comprising the steps of:
  (a) subjecting a root material of *Zanthoxylum avicennae* (Lam.) DC. to an acid treatment using a first acid solution under heating such that an acid-treated root material of *Zanthoxylum avicennae* (Lam.) DC. is obtained;
  (b) subjecting the acid-treated root material of *Zanthoxylum avicennae* (Lam.) DC. to an extraction treatment using an alcohol solution such that an alcohol-extracted product is obtained; and
  (c) admixing the alcohol-extracted product with a second acid solution such that the product is formed.

2. The product as claimed in claim 1, wherein in step (a) of the process, the root material of *Zanthoxylum avicennae* (Lam.) DC. is root skin of *Zanthoxylum avicennae* (Lam.) DC.

3. The product as claimed in claim 1, wherein the first and second acid solutions are independently selected from the group consisting of vinegar, acetic acid, formic acid, lactic acid, malic acid, oxalic acid, and citric acid.

4. The product as claimed in claim 1, wherein in step (b) of the process, the alcohol solution is selected form the group consisting of methanol, ethanol, propanol, isopropanol, n-butanol, and isobutanol.

5. A pharmaceutical composition comprising a product containing an extract from *Zanthoxylum avicennae* (Lam.) DC. as claimed in claim 1.

6. A process for preparing a product containing an extract from *Zanthoxylum avicennae* (Lam.) DC., comprising the steps of:
   (a) subjecting a root material of *Zanthoxylum avicennae* (Lam.) DC. to an acid treatment using a first acid solution under heating such that an acid-treated root material of *Zanthoxylum avicennae* (Lam.) DC. is obtained;
   (b) subjecting the acid-treated root material of *Zanthoxylum avicennae* (Lam.) DC. to an extraction treatment using an alcohol solution such that an alcohol-extracted product is obtained; and
   (c) admixing the alcohol-extracted product with a second acid solution such that the product is formed.

7. The process as claimed in claim 6, wherein in step (a), the root material of *Zanthoxylum avicennae* (Lam.) DC. is root skin of *Zanthoxylum avicennae* (Lam.) DC.

8. The process as claimed in claim 6, wherein the first and second acid solutions are independently selected from the group consisting of vinegar, acetic acid, formic acid, lactic acid, malic acid, oxalic acid, and citric acid.

9. The process as claimed in claim 6, wherein in step (b), the alcohol solution is selected form the group consisting of methanol, ethanol, propanol, isopropanol, n-butanol, and isobutanol.

10. A method of treating a cancer in a subject, comprising administering to the subject a pharmaceutical composition comprising an effective amount of the product of claim 1.

11. The method as claimed in claim 10, wherein the cancer is liver cancer.

12. A method of inhibiting tumor/cancer cells, comprising contacting the cells with an effective amount of the product of claim 1.

13. The method of claim 12, wherein the inhibition of tumor/cancer cells includes inhibition of cell proliferation, inhibition of cell metastasis, and induction of apoptosis.

14. The method as claimed in claim 12, wherein the tumor/cancer cells are liver cancer cells.

\* \* \* \* \*